Figure 1:
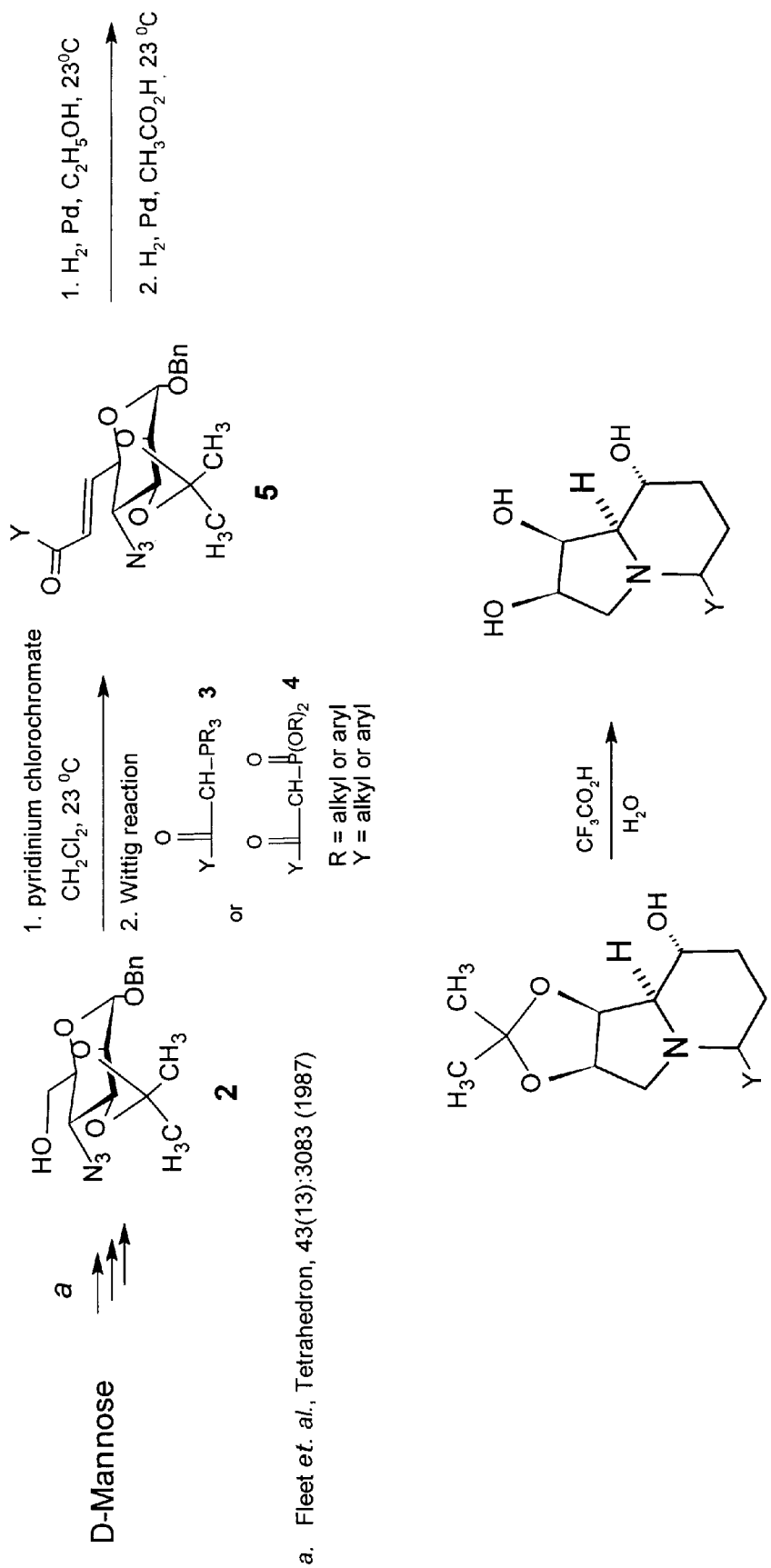
Figure 2:
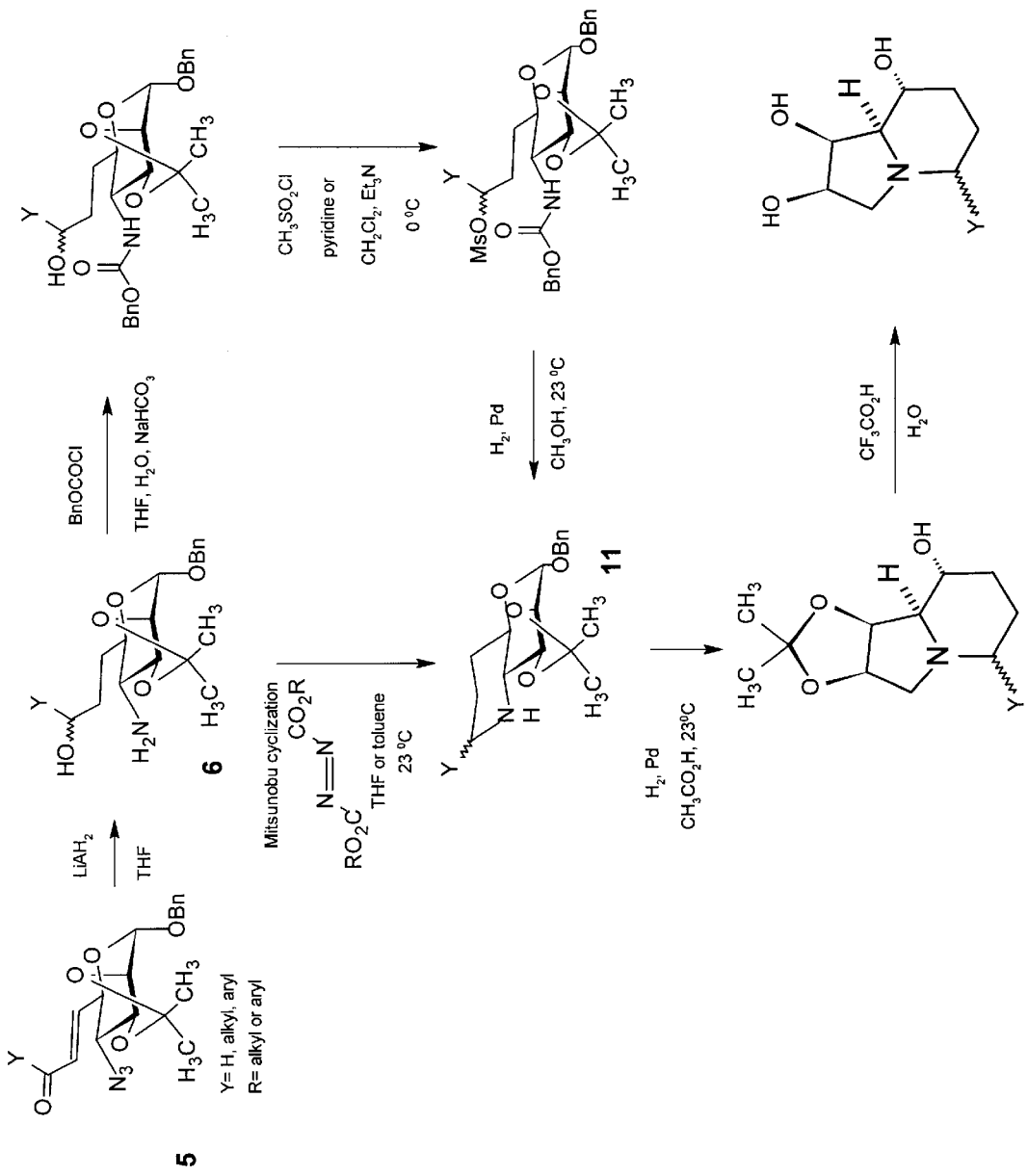
Figure 3A:
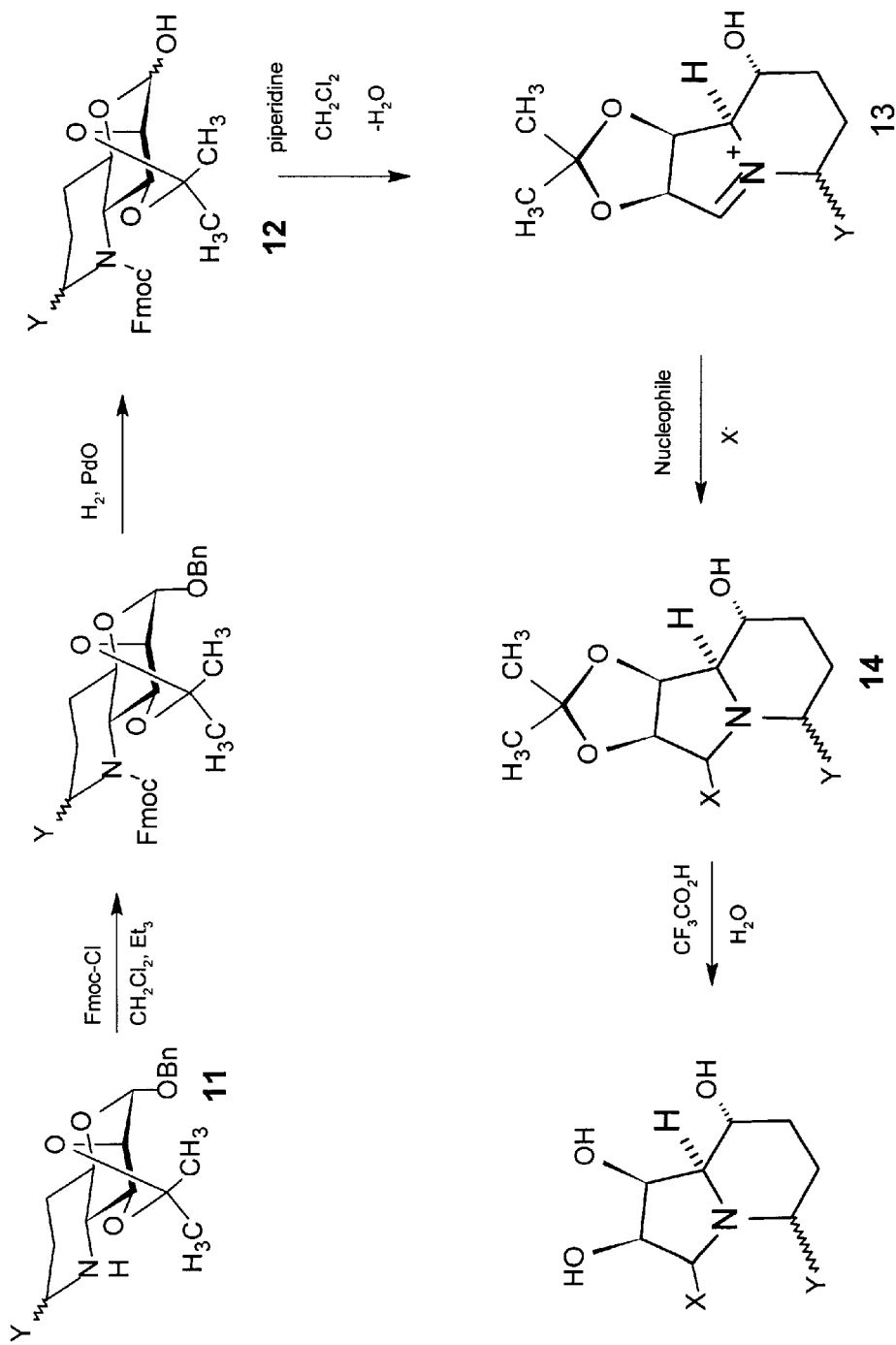
Figure 3B:
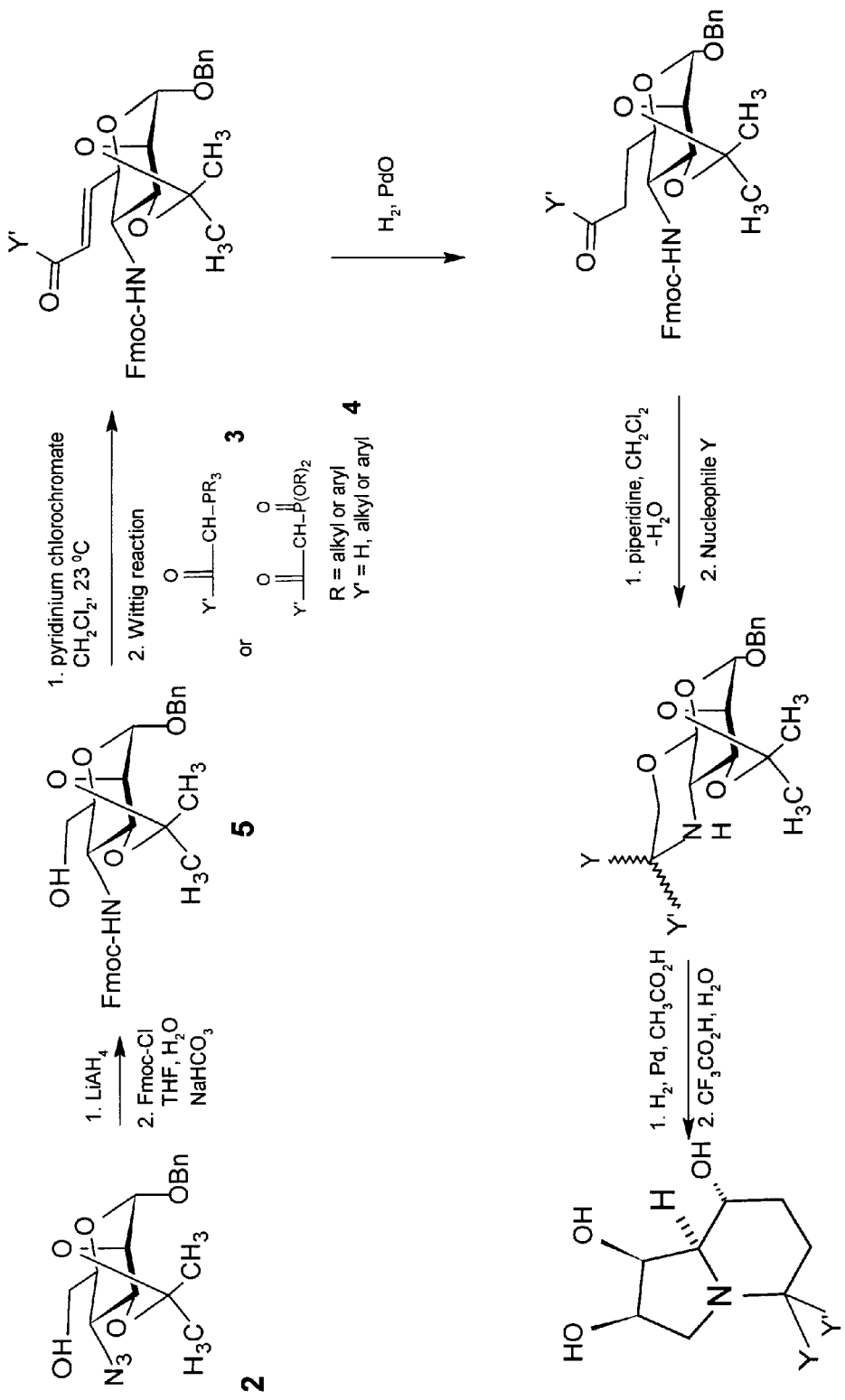
Figure 4:
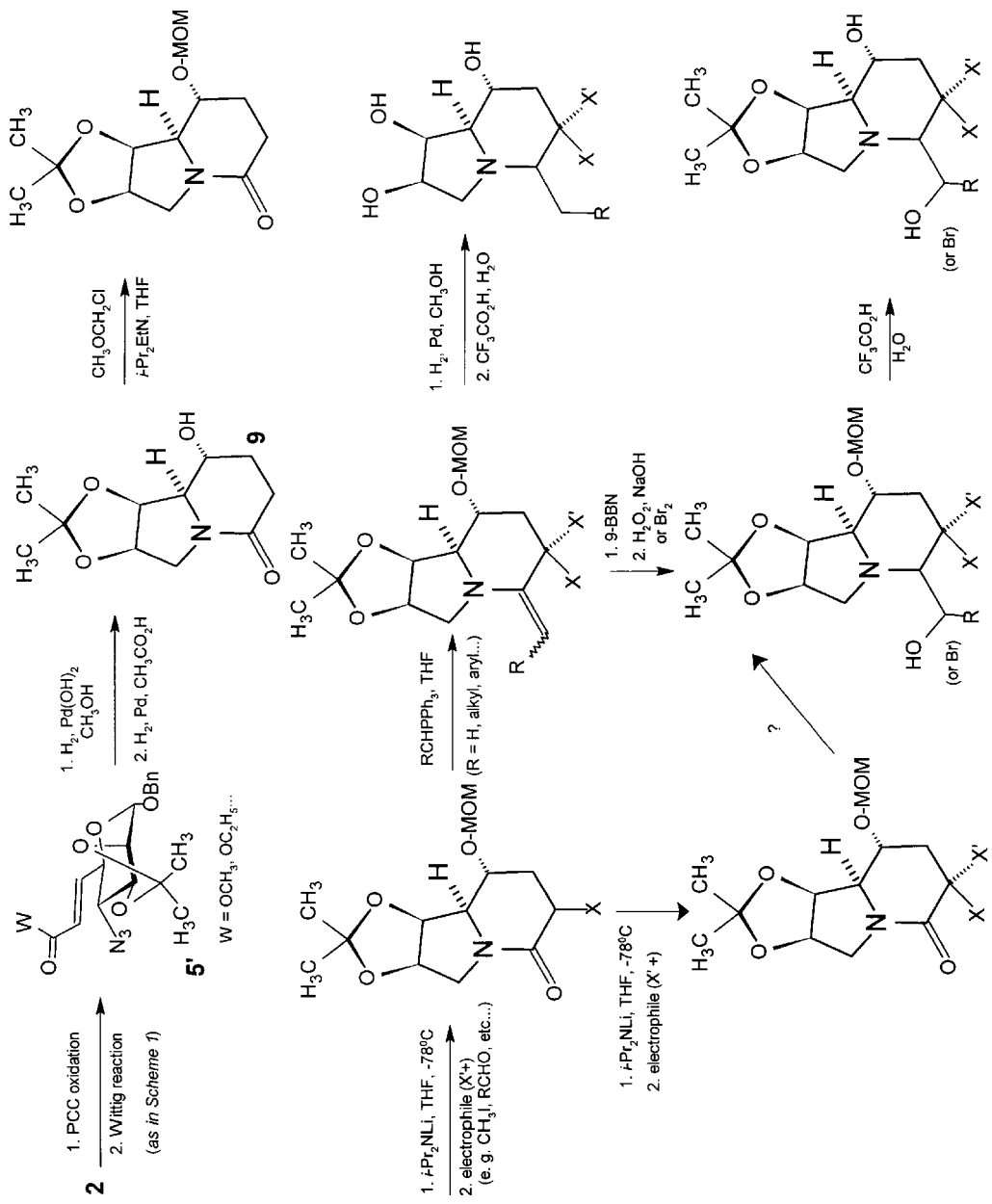
Figure 5:
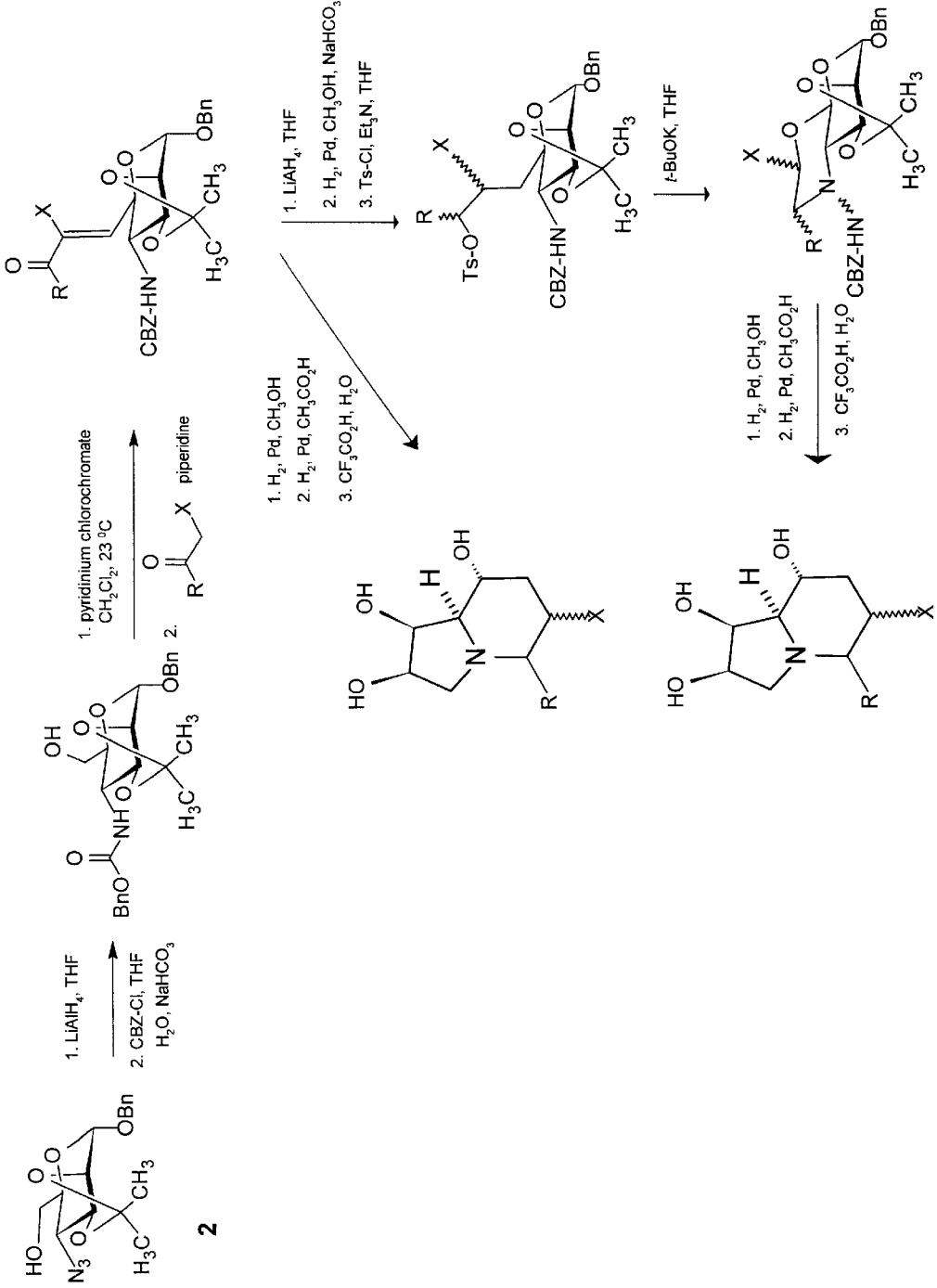
Figure 6:
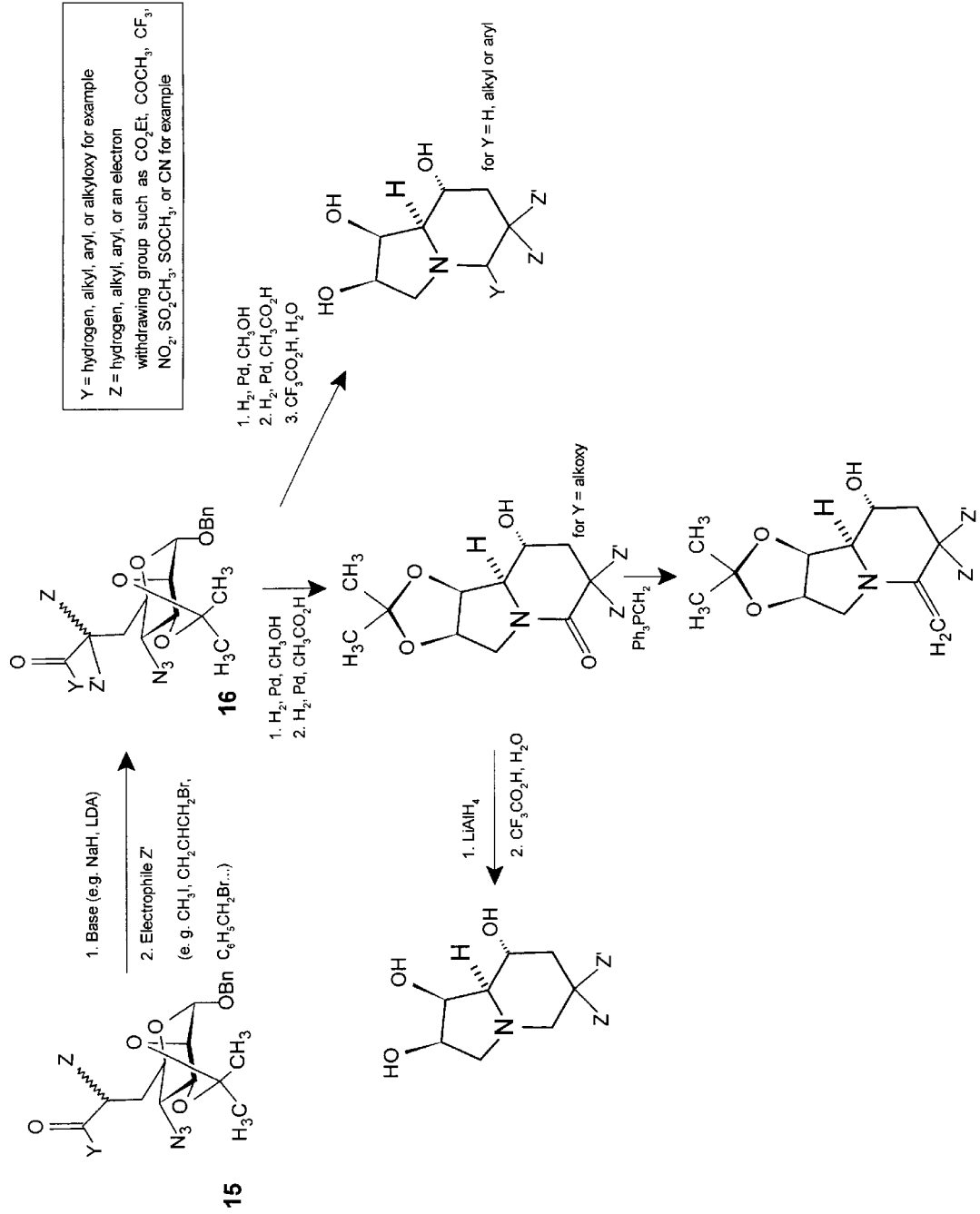
Figure 7:
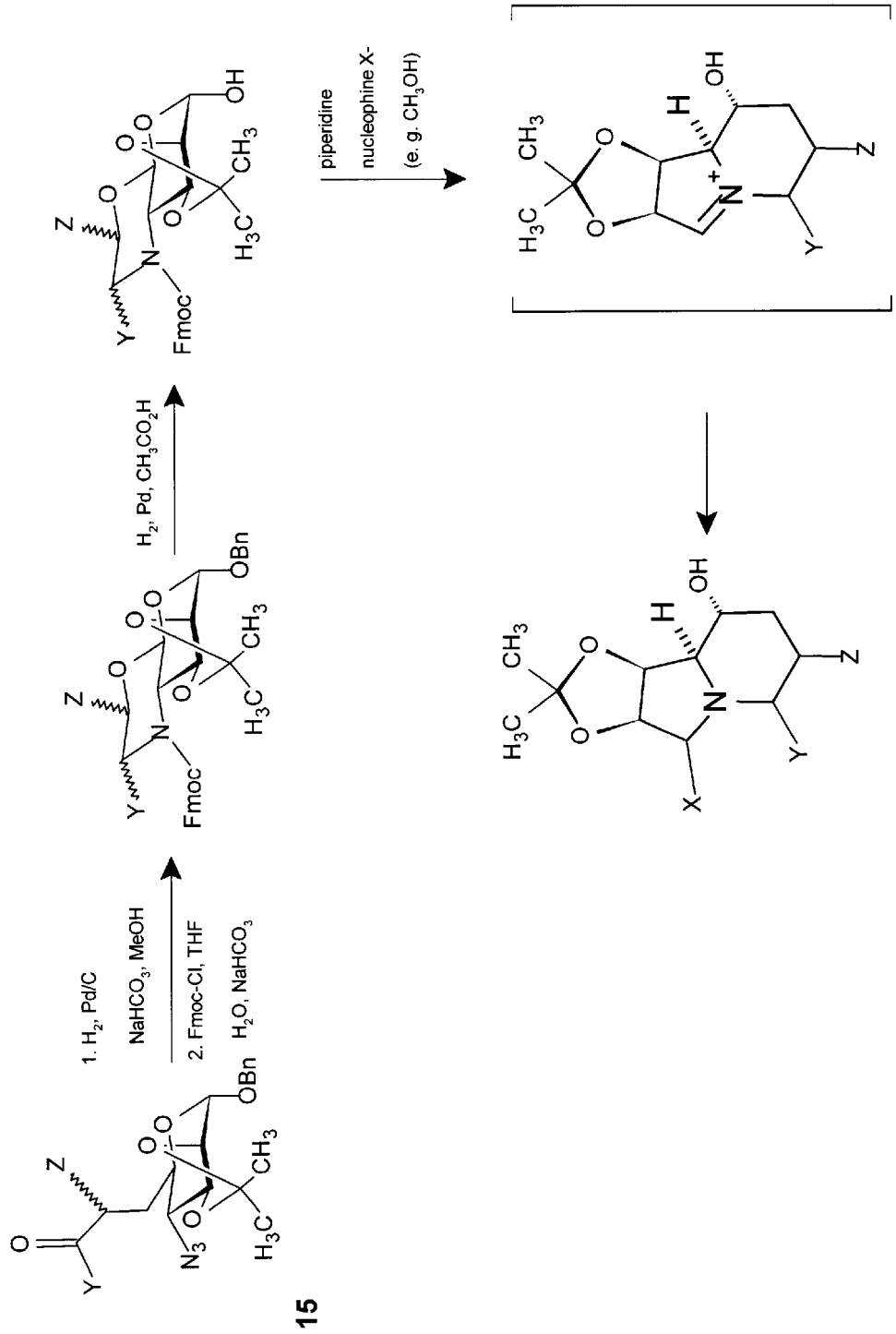

US006048870A

United States Patent [19]
Shah et al.

[11] Patent Number: 6,048,870

[45] **Date of Patent: *Apr. 11, 2000**

[54] 3, 5, AND/OR 6 SUBSTITUTED ANALOGUES OF SWAINSONINE PROCESSES FOR THEIR PREPARATION AND THEIR USE AS THERAPEUTIC AGENTS

[75] Inventors: Rajan Shah; Jeremy Carver, both of Toronto; Jose Marino-Albernas, Vancouver; Igor Tvaroska, Toronto; Francois Tropper, Toronto; James Dennis, Toronto, all of Canada

[73] Assignee: GlycoDesign, Toronto, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/941,689

[22] Filed: Oct. 1, 1997

Related U.S. Application Data

[60] Provisional application No. 60/027,585, Oct. 3, 1996, and provisional application No. 60/027,791, Oct. 1, 1996.

[51] Int. Cl.[7] ...................... C07D 471/04; A61K 31/435

[52] U.S. Cl. ........................................... 514/299; 546/112

[58] Field of Search .................................. 546/121, 112; 514/299

[56] References Cited

U.S. PATENT DOCUMENTS

| | | | |
|---|---|---|---|
| 3,274,202 | 9/1966 | Mohrbacher | 514/299 |
| 4,792,558 | 12/1988 | Sunkara et al. | 514/299 |
| 4,837,237 | 6/1989 | Rohrschneider et al. | 514/62 |
| 4,857,315 | 8/1989 | Dennis | 424/85.2 |
| 4,894,388 | 1/1990 | Fleet | 574/425 |
| 4,996,329 | 2/1991 | Fleet et al. | 548/453 |
| 5,021,427 | 6/1991 | Elbein et al. | 514/299 |
| 5,023,340 | 6/1991 | Fleet | 548/453 |
| 5,041,555 | 8/1991 | Fleet et al. | 548/541 |
| 5,075,448 | 12/1991 | Fleet | 546/112 |
| 5,075,457 | 12/1991 | Fleet | 548/453 |
| 5,187,279 | 2/1993 | Cha et al. | 546/183 |
| 5,264,356 | 11/1993 | Rohrschneider | 514/425 |
| 5,272,070 | 12/1993 | Lehrman et al. | 435/172.1 |
| 5,288,875 | 2/1994 | Cha et al. | 548/453 |
| 5,376,675 | 12/1994 | Alphey et al. | 514/425 |
| 5,382,709 | 1/1995 | Farr et al. | 368/704 |
| 5,438,069 | 8/1995 | Farr et al. | 514/1 |
| 5,466,809 | 11/1995 | Dime | 546/183 |
| 5,484,925 | 1/1996 | Cha et al. | 546/90 |
| 5,621,106 | 4/1997 | Dime | 546/183 |
| 5,633,261 | 5/1997 | Dime | 514/299 |
| 5,650,413 | 7/1997 | Carver et al. | 514/299 |
| 5,780,633 | 7/1998 | Okada et al. | 546/112 |

FOREIGN PATENT DOCUMENTS

| | | |
|---|---|---|
| 2040058 | 10/1991 | Canada . |
| 1298549 | 4/1992 | Canada . |
| 004260 | 3/1979 | European Pat. Off. . |
| 0004260 | 10/1979 | European Pat. Off. . |
| 0036269 | 9/1981 | European Pat. Off. . |
| 0104826 | 4/1984 | European Pat. Off. . |
| 0295538 | 12/1988 | European Pat. Off. . |
| 0424349 | 4/1991 | European Pat. Off. . |
| 0451834 | 10/1991 | European Pat. Off. . |
| 3507019 | 8/1986 | Germany . |
| 61277685 | of 0000 | Japan . |
| 60-218389 | 4/1984 | Japan . |
| 60-16680 | 8/1985 | Japan . |
| 60-193986 | 10/1985 | Japan . |
| 61-227566 | 9/1986 | Japan . |
| WO9006311 | 6/1990 | WIPO . |
| WO93/05040 | 3/1993 | WIPO . |
| WO93/05781 | 4/1993 | WIPO . |
| WO9309117 | 5/1993 | WIPO . |
| WO9535094 | 12/1995 | WIPO . |
| WO9640683 | 12/1996 | WIPO . |

OTHER PUBLICATIONS

Dennis J. W. in "Cell Surface Carbohydrates and Cell Development", Fukuda M.(ed)., CRC Press, Boca Raton, Ann Arbor London, 1992, Chapter 6, pp. 161–194.

Dennis J. W. et al, Science, 236:582, 1987.

VanderElst, E. and J.W. Dennis, Experimental Cell Research 192: 612–621, 1991.

J.W. Dennis, Cancer Research 46:5131, 1986.

Humphries, M.J. et al, Proc.Natl. Acad, Sci, USA, 83:1752, 1986.

Colegate S.M. et al., Aust. J. Chem. 1979, 32: 2257–64, 1979.

Molyneux R.J. and L.F. James, Science 216:190, Apr. 1982.

Schneider M.J. et al, Tetrahedron 39(1):29, 1983.

Tulsiani D.R.P. et al, J. Biol. Chem. 257:7936, 1982.

Fernandes, B. et al, Cancer Research 51: 718, 1991.

Olden K. et al, Pharmac. Ther. 50:285, 1991.

Humphries, M.J. et al, Cancer Research 48:1410, 1988.

M. Yagita and E. Sakela, Scand. J. Immunol 31:275–282, 1990.

White, S.L. et al, Biochem Biophys. Res. Commun. 150:615–625, 1988.

Seftor, R.E.B. Melanoma Research 1:43–54, 1991.

Yagel S., et al., Intl. J. Cancer 44:685, 1989.

J.W. Dennis et al, J. Natinal Cancer Institute 81:1028, 1989.

J.W. Dennis et al, Cancer Research 50:1867, 1990.

Humphries, M.J. and K. Olden, Pharmac. Ther. 44:85–105, 1989.

White, S.L. et al., Cancer Communications, 3(30):83, 1991.

Oredipe, O.A., et al, J. National Cancer Institute, 83:1149, 1991.

J.W. Dennis, et al, Biochemical Pharmacology 46:1459, 1993.

(List continued on next page.)

*Primary Examiner*—Zinna Northington Davis
*Attorney, Agent, or Firm*—Merchant & Gould P.C.

[57] ABSTRACT

The invention relates to novel 3, 5, and/or 6 swainsonine analogues, processes for their preparation and their use as therapeutic agents. The invention also relates to pharmaceutical compositions containing the compounds and their use as therapeutics.

30 Claims, 8 Drawing Sheets

OTHER PUBLICATIONS

Aoyama, H. et al, J. Org. Chem. 57:3027–3041, 1992.
Hibbett, E. P., and J. Sam, J. Het. Chem. 7:857,1970.
Heidt, P.C. et al, Tetrahedron Letters 31: 5441, 1990.
Reinecke, M., and L.R. Kray, J. Org. Chem. 29: 1736, 1964.
Chastanet, J. and G. Roussi, J. Org, Chem, 50:2910–2914, 1985.
Bashyal, B.P. et al, Tetrahedron Letters, 3083,1987.
Clemo, G.R. and T.P. Metcalfe, J. Chem. Soc. 1937, p. 1518.
Leonard, N.J. et al, J. Org. Chem. 22:1445, 1957.
Winkler D.A. and G. Holan, J. Med. Chem., 32:2084, 1989.
Reinecke, M.G. and L.R. Kray, J. Org. Chem 30:3671, 1965.
Bogeso, K.P. et al, J. Med. Chem. 30:142–150, 1987.
Goss P.E. et al, Cancer Res. 54: 1450, 1994.
Hino et al, J. Antibiot. (Tokyo) 38: 926–935, 1985.
Goss, P.E. et al, Clin. Cancer Res. 3:1077,1997.
Holden R.T. and R. Raper, J. Chem. Soc. p. 2545, 1963.
Biniecki S. et al., Chemical Abstracts, 1984, 101, No. 90743a.
Biniecki, S. et al., Chemical Abstracts, 106, 1987, 138204h.
Boegesoe, K. P., et al., Chemical Abstracts, 106, 1987, No. 84369v.
Smith, M.B. et al., Chemical Abstracts vol. 104, 1986, No. 51007f.
Hashimoto, S. et al., Chemical Abstracts vol. 106, 1987, No. 138253y.
Miyano, Se. et al, Chemical Abstracts, vol. 98, 1983, No. 179148c.
Yoon, U.C. et al., Chemical Abstracts vol. 97, 1982, No. 38827r.
Fujiwara, et al, Chemical Abstracts vol. 117, 1992, No. 211862e.
Winterfeld, K. et al., Chemical Abstracts vol. 74, 1971, No. 3456s.
Motohiro, et al., Chemical Abstracts vol. 101, Abstract 28283x, 1984.
Temple Jr. C. and G. Rener, J. Med Chem 32:2089, 1989.
Nicolson, G.L. Biochem Biophys. Acta. 695:113, 1982.
Tulsiani, D.R.P. et al., Archives Biochem. Biophys. 232: 76–85, 1984.
Levine, A.S. et al., Can. Res. 39: 1645–1650, 1970.
Bowlin, T.L. et al., Cancer Research 49:4109–4113, 1989.
Tulsiani, D.R.P. and O. Touster, J. Biol. Chem., 258: 7578–7585, 1983.
S.R. Wilson and R.A. Sawicki J. Org. Chem 44:330, 1979.
Villiani et al, J. Org. Chem., 6:142, 1962.
Austin, G.N. et al, Tetrahedron, 43:3095–3108, 1987.
Skelton, B.W. and White, A.H., Aust. J. Chem. 33:435–9, 1980.
Pearson, W. H. and E.J. Hembre, J. Org. Chem. 61:5546–5556, 1996.
Rodriguez, R. and F. Bermejo, Tetrahedron Letters 37: 5581–5584, 1996.
Keck, G. E. and D.R. Romer, J. Org. Chem. 58: 6083–6089, 1993.
Kim Y.G., and J.K. Cha, Tetrahedron Letters, 30:5721–5724, 1989.
Tadano, K. et al, J. Org Chem,. 53:5209–5215, 1988.
Tadano, K., et al, Bull Chem. Soc. Jpn. 59: 3885–3892, 1986.
Tadano, K., et al, Bull. Chem. Soc. Jpn., 60:3667–3671, 1987.
Honda, T. et al, Chem. Soc. Perkin Trans. 1, p. 2091, 1994.
Suami, T. et al, Chemistry Letters, pp. 513–516, 1984.
Hembre, E.J. and W. H. Pearson, Tetrahedron 53: 11021–11032, 1997.
Fleet, G.W.J. et al., Tetrahedron Letters 26: 3127–3130, 1985.
Fleet, G.W.J. et al, Tetrahedron 44:2649, 1988.
Demetriou M. et al, J. Cell Biol. 130:383–392, 1995.
Dennis et al., Oncogene 4:853–860, 1998.
Bennett R.B. et al, J. Org. Am. Chem. Soc. 111:2580–2582, 1989.
The Alkaloids, vol. 44, Chapter 3, Simple Indolizidine Alkaloids, Hiroki Takahata and Takefumi Momose, 1993, Academic Press.
J. Am. Chem. Soc., Enantiomerically Pure Polyhydroxylated Acyliminium Ions, Synthesis of the Glycosidase Inhibitors (−) Swainsonine and (+) Castanospermine, Scott A. Miller and Richard Chamberlin, 1990, 112, pp. 8100–8112.
J. Org. Chem, A Practical Synthesis of (−) Swainsonine, William H. Pearson and Erik J. Hembre, 1996, 61, pp. 7217–7221.
Enantiospecific Syntheses of Leukotrienes $C_4$, $D_4$, and $E_4$ and $[14,15-{}^3H_2]$ Leukotriene $E_4$ Dimethyl Ester, Cohen et al, 1983 American Chemical Society.
2,3–0–Isopropylidene–D–Erythronolactone, Cohen et al., Org. Synth., (1985), 63, pp. 127–135.
The Chemistry of Castanospermine, Part IV[1]: Synthetic Modifications at C–8. Furneaux et al., Tetrahdron vol. 51, No. 46, pp. 12611–12630, 1995.
Synthesis of Novel Glycosidase–Inhibitory Hydroxymethyl–Substituted Polyhydroxylated Indolizidines: Ring–Expanded Analogs of the Pyrrolizidine Alkaloids Alexine and Australine, Pearson et al., J. Org. Chem., 1996, 61, pp. 5546–5556.
Synthesis of the Mannosidase Inhibitors Swainsonine and 1,4–Dideoyx–1,4–Imino–D–Mannitol and of the Ring Contracted Swainsonine (1S,2R,7R,7aR)–1,2,7–Trihydroxypyrrolidine and (1S,2R,7S,7aR)–1,2,7–Trihydroxypyrrolizidine, Carpenter et al., Tetrahedron Letters, vol. 30, No. 51, pp. 7261–7264, 1989.

a. Fleet et. al., Tetrahedron, 43(13):3083 (1987)

3, 5, AND/OR 6 SUBSTITUTED ANALOGUES OF SWAINSONINE PROCESSES FOR THEIR PREPARATION AND THEIR USE AS THERAPEUTIC AGENTS

This application claims as priority provisional application No. 60/027,585 filed Oct. 3, 1996 and provisional application No. 60/027,791 filed Oct. 1, 1996.

FIELD OF THE INVENTION

The present invention relates to novel analogues of swainsonine, processes for their preparation and their use as therapeutic agents.

BACKGROUND OF THE INVENTION

Carbohydrate structures present on human tumor cells have been associated with cancer invasion and metastasis (Dennis et. al., *Science* 236: 582, 1987; Demetriou et al., *J. Cell Biol.* 130:383, 1995). These structures include the GlcNAc β(T1-6) branched N- and O-linked carbohydrate side chains of cell-surface glycoproteins. The Golgi enzymes required for their synthesis are β(T1-6) N-acetylglucosaminyltransferase V (i.e. GlcNAc-TV) and core 2 β(T1-6) N-acetylglucosaminyltransferase (i.e. core 2 GlcNAc-T), respectively. These enzymes are up-regulated in human carcinomas (Fernandes et al., Cancer Res. 51:718–723, 1991), a phenomenon that has been associated with the activation of the ras signaling pathway (Dennis et al., Science 236:582–585, 1987; Dennis et al Oncogene 4:853–860, 1989)). Furthermore, overexpression of GlcNAc-TV in epithelial cells results in morphological transformation and tumor formation in mice (Demetriou et al, J. Cell Biol. 130:383–392, 1995). Therefore, GlcNAc-TV as well as enzymes supplying acceptor substrates to GlcNAc-TV (i.e. GlcNAc-TI, α-mannosidase II and core 2 GlcNAc-T of the O-linked pathway) are targets for anti-cancer pharmaceuticals.

Although there are no inhibitors of GlcNAc-TV presently available, a lead α-mannosidase II inhibitor, swainsonine has been tested in preclinical and human trials. Swainsonine is an indolizidine alkaloid found in Australian *Swainsona canescens* (Colegate et al., Aust J Chem 32:2257–2264, 1979), North American plants of the genera Astragalus and Oxytropis (Molyneux R J and James L F., Science 215:190–191, 1981), and also the fungus *Rhizoctonia leguminicola* (Schneider et al., Tetrahedron 39;29–31, 1983). Swainsonine's ability to inhibit α-mannosidase II activity appears to be responsible for its interesting immunomodulating and cancer suppression activity. Swainsonine is believed to function as an enzyme inhibitor because it can mimic the glycosylium cation intermediate generated during the hydrolytic cleavage of mannopyranosides. (Goss, P. E. et al., *Clin. Cancer Res.* 1: 935–944, 1995).

The swainsonine blockage of α-mannosidase II is prior to GlcNAc-TV and prevents expression of GlcNAc β(T1-6) branched N-linked carbohydrates. Swainsonine-treated murine tumor cells have been found to be less metastatic in both organ-colonization and spontaneous metastasis assays in mice (Dennis J. W., Cancer Res. 46:5131–5136, 1986 and Humphries et al., Proc. Natl. Acad. Sci. U.S.A. 83:1752–1756, 1986). Swainsonine has also been shown to block tumor cell invasion through extracellular matrix in vitro (Yegel et al., Int. J. Cancer 44:685–690, 1989 and Seftor et al., Melanoma Res. 1:53–54, 1991). Swainsonine administered either orally or by mini-osmotic pumps to athymic nude mice inhibited the growth rate of human MeWo melanoma and HT29m colon carcinoma tumor xenografts in the mice (Dennis et al., J. Natl. Cancer Inst. 81:1028–1033, 1989 and Dennis et al., Cancer Res., 50:1867–1872, 1990).

Phase I clinical trials of swainsonine have been done which indicate that it has efficacy in the treatment of human tumors. (Goss et. al, *Cancer Res.,* 54:1450, 1995). Although side-effects in humans are mild, some of these may be associated with swainsonine's inhibition of lysosomal storage of carbohydrates.

Swainsonine has positive effects on cellular immunity in mice (reviewed in Humphries M. J. and Olden K., Pharmacol Ther. 44:85–105, 1989, and Olden et al., Pharmacol Ther 50:285–290, 1991)). In particular, swainsonine has been shown to alleviate both chemically-induced and tumor-associated immune suppression (Hino et al., J. Antibiot. (Tokyo) 38:926–935, 1985), increase NK cell (Humphries et al., Cancer Res. 48:1410–1415, 1988), and LAK cell activities (Yagita M and Saksela E., Scand. J. Immunol. 31:275–282, 1990), and increase splenic and bone marrow (BM) cell proliferation (White et al., Biochem. Biophys. Res. Commun. 150;615–625, 1988; Bowlin et al. Cancer Res 49, 4109–4113, 1989, and White et al., Cancer Commun. 3:83–91, 1991). SW has also been shown to be hemorestorative in mice following treatment with both cycle-specific and nonspecific chemotherapeutic agents (Oredipe et al., J. Natl. Cancer Inst. 83:1149–1156, 1991).

Japanese Patent Application No. J61277685 describes indolizidine derivatives which are reported to be useful as immune regulators, which can be administered orally or parenterally at a dose of about 0.1–100 ml/kg a day. It is also reported that the indolizidine derivatives may be used in combination with antitumour agents, antimicrobial agents or antiinflammatories.

Carbonoyloxy substitutions at the 2 and 8 carbons of swainsonine have been reported to reduce inhibitor activity by 2–3 orders of magnitude for Jack Bean and MDAY-D2 tumor cell lysosomal mannosidases in vitro. However, 2-p-nitrobenzoyloxy, 2-octanoyloxy- and 2-butanoyloxy-derivatives of swainsonine retained full activity as inhibitors of Golgi oligosaccharide processing in viable MDAY-D2 tumor cells. Inhibition of oligosaccharide processing was reduced by the esterase inhibitor diethyl p-nitrophenyl phosphate, suggesting that while the compounds are relatively poor inhibitors of mannosidase in vitro, the compounds enter cells at a rate comparable to that of swainsonine and are converted to swainsonine by cellular esterases. The more lipophilic esters, 2-benzoyloxy-swainsonine, 2-toluoyloxy-swainsonine, 8-palmitoyloxy-swainsonine and 8-myristinoyloxy-swainsonine, showed $IC_{50}$ values at least 10 times higher for inhibition of Golgi oligosaccharide processing, probably due to less efficient entry of the compounds into tumor cells. The anti-metastatic activities of swainsonine and two analogs were tested and shown to correlate with the $IC_{50}$ values for inhibition of Golgi oligosaccharide processing in cultured tumor cells. In vivo, SW and the analogues were administered intraperitoneally to mice and found to have comparable activities as stimulators of bone marrow cell proliferation. (Dennis, J. W. et al. Biochemical Pharmacology 46:1459–1466, 1993).

Selected swainsonine analogues, in particular 2-substituted analogues, and methods for preparing the analogues are described in U.S. Pat. No. 5,466,809.

SUMMARY OF THE INVENTION

The present inventors have studied the profiles of reactions catalyzed by mannosidase inhibitors, atomic charge distributions in the mannopyranosyl cation (an intermediate in the reaction catalyzed by mannosidases) and swainsonine derivatives, and the chemical topography of the mannosidase II binding pocket. They found that analogues of swainsonine which more closely mimick the true transition state species (i.e. mannopyranosyl cation) rather than the mannosylium cation intermediate, provided improved inhibitory potency. In particular, selective derivatization of swainsonine at one or both of positions 3 and 5 with electron withdrawing groups provided analogues of swainsonine which are ideally suited for use as drugs and prodrugs having improved pharmacological properties. The present inventors have also found that selective derivatization at the 6 position also provides analogues which having improved pharmacological properties.

The present invention therefore relates to a compound of the formula I

I wherein (1) $R^1$, $R^2$ and $R^3$ are the same or different and represent hydrogen, alkyl, cycloalkyl, alkenyl, alkynyl, unsaturated monocyclic hydrocarbons, aryl, or $R^1$ and $R^2$ together or $R^2$ and $R^3$ together form a carbocyclic or heterocylic ring;

(2) W, W' and W" are the same or different and represent hydroxyl, alkoxy, thiol, thioalkyl, thioaryl, halo or amino, or one or more of W and W" and W' and W" together form a carbocyclic or heterocyclic ring; or one or more of $R^1$ and W, $R^2$ and W', and $R^3$ and W" form a spiro ring system;

(3) X, X', Y, Y', Z, and Z' are the same or different and represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epooxide, alkoxy or aryloxy amines, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —$SR^9$ wherein $R^9$ is alkyl, cycloalkyl, alkenyl, alkynyl, or unsaturated monocyclic hydrocarbons, and —OR where R is alkyl is alkyl, cycloalkyl, alkenyl, alkynyl, or unsaturated monocyclic hydrocarbons; or (i) X and Y, X' and Y, X' and Y, or X' and Y' may together form a carbocyclic, or heterocyclic ring, or Y and Z, Y and Z', or Y' and Z' may together form a carbocyclic, or heterocyclic ring;

(ii) one or more of X and X' together, Y and Y' together, and Z and Z' together may form a spiro ring; or (iii) one or more of X and X' together, Y and Y' together, and Z and Z' together represent =O, =S, or $=NR^4$ wherein $R^4$ is hydrogen, alkyl, cycloalkyl, alkenyl, alkynyl, unsaturated monocyclic hydrocarbons, aryl, alkoxy, hydroxyl, or $=CR^5R^6$ wherein $R^5$ and $R^6$ are the same or different and represent hydrogen, alkyl, cycloalkyl, alkenyl, alkynyl, cycloalkenyl, cycloalkynyl unsaturated monocyclic hydrocarbons, or aryl;

with the proviso that X, X', Y, Y', and Z, Z' cannot all be hydrogen, and salts and optically active and racemic forms of a compound of the formula I.

In an embodiment of the invention, compounds of the formula I are provided wherein when $R^1$, $R^2$, $R^3$, X, X', Y, Y' are hydrogen, W, W', and W" are not hydroxyl. In another embodiment of the invention, compounds of the formula I are provided wherein when $R^1$, $R^2$, $R^3$, X, X', Z and Z' are hydrogen, and W, W', and W" are hydroxyl, Y and Y' together cannot be =O or one of Y and Y' cannot be alkoxy.

The present invention also provides a process for the preparation of a compound of the formula I as defined herein, and a pharmaceutical formulation comprising a compound of the formula I as an active agent.

The invention further relates to a method for stimulating the immune system, treating proliferative disorders, or microbial infections in a patient comprising administering an effective amount of a compound of the formula I of the invention. The invention also relates to the use of a compound of the formula I in the preparation of a medicament for stimulating the immune system, and/or for treating proliferative disorders, and microbial infections.

The present invention also relates to the use of a compound of the formula I which is esterified at free hydroxyls as a prodrug.

These and other aspects of the present invention will become evident upon reference to the following detailed description and attached drawing. In addition, reference is made herein to various publications, which are hereby incorporated by reference in their entirety.

BRIEF DESCRIPTION OF THE DRAWINGS

The invention will be better understood with reference to the drawings in which:

FIG. 1 is a schematic diagram of a reaction for preparing a novel analogue of the invention;

FIG. 2 is a schematic diagram of a reaction for preparing a novel analogue of the invention;

FIG. 3A is a schematic diagram of a reaction for preparing a novel analogue of the invention;

FIG. 3B is a schematic diagram of a reaction for preparing a novel analogue of the invention;

FIG. 4 is a schematic diagram of a reaction for preparing a novel analogue of the invention;

FIG. 5 is a schematic diagram of a reaction for preparing a novel analogue of the invention;

FIG. 6 is a schematic diagram of a reaction for preparing a novel analogue of the invention; and FIG. 7 is a schematic diagram of a reaction for preparing a novel analogue of the invention.

DETAILED DESCRIPTION OF THE INVENTION

1. Compounds of the Invention

Hereinabove and in the following the term "alkyl", alone or in combination, refers to a branched or linear hydrocarbon radical, typically containing from 1 through 20 carbon atoms, preferably 1 through 15. Typical alkyl groups include but are not limited to methyl, ethyl, 1-propyl, 2-propyl, 1-butyl, 2-butyl, tert-butyl, pentyl, hexyl, and the like.

The term "alkenyl", alone or in combination, refers to an unsaturated branched or linear group typically having from 2 to 20 carbon atoms and at least one double bond. Examples of such groups include but are not limited to ethenyl, 1-propenyl, 2-propenyl, 1-butenyl, 1,3-butadienyl, hexenyl, pentenyl, and the like.

The term "alkynyl", alone or in combination, refers to an unsaturated branched or linear group having 2 to 20 carbon atoms and at least one triple bond. Examples of such groups include but are not limited to ethynyl, 1-propynyl, 2-propynyl, 1-butynyl, 2-butynyl, 1-pentynyl, and the like.

The term "cycloalkyl" refers to cyclic hydrocarbon groups and includes but is not limited to cyclopropyl, cyclobutyl, cyclopentyl, cyclohexyl, cycloheptyl, and cyclooctyl.

The terms "cycloalkenyl" and "cycloalkynyl" refer to unsaturated monocyclic hydrocarbons having one endocyclic double or one triple bond. Compounds of the formula I having more than one such multiple bond are cycloalkadienyl, cycloalkatrienyl, etc. The inclusive term for any cyclic hydrocarbons having any number of such multiple bonds is unsaturated monocyclic hydrocarbons. Examples of unsaturated monocyclic hydrocarbons are cyclohexene, cyclopentadiene, and cyclooctadiene.

The term "aryl", alone or in combination, refers to a monocyclic or polycyclic group, preferably a monocyclic or bicyclic group. An aryl group may optionally be substituted as described herein. Examples of aryl groups and substituted aryl groups are phenyl, benzyl, p-nitrobenzyl, p-methoxybenzyl, biphenyl, and naphthyl.

The term "alkoxy" alone or in combination, refers to an alkyl or cycloalkyl linked to the parent molecular moiety through an oxygen atom. The term "aryloxy" refers to an aryl linked to the parent molecular moiety through an oxygen atom. Examples of alkoxy groups are methoxy, ethoxy, propoxy, vinyloxy, allyloxy, butoxy, pentoxy, hexoxy, cyclopentoxy, and cyclohexoxy. Examples of aryloxy groups are phenyloxy, O-benzyl i.e. benzyloxy, O-p-nitrobenzyl and O-p-methyl-benzyl, 4-nitrophenyloxy, 4-chlorophenyloxy, and the like.

The term "halo" or "halogen", alone or in combination, refers to a member of the family fluorine, chlorine, bromine, or iodine.

The term "amino", alone or in combination, refers to a chemical functional group where a nitrogen atom (N) is bonded to three substituents being any combination of hydrogen, alkyl, cycloalkyl, alkenyl, alkynyl, unsaturated monocyclic hydrocarbons, or aryl with the general chemical formula —NR$^7$R$^8$ where R$^7$ and R$^8$ can be any combination of hydrogen, alkyl, cycloalkyl, alkenyl, alkynyl, unsaturated monocyclic hydrocarbons, or aryl. Optionally one substituent on the nitrogen atom can be a hydroxyl group (—OH) to give an amine known as a hydroxylamine. Examples of amino groups are amino (—NH$_2$), methylamine, ethylamine, dimethylamine, cyclopropylamine, benzylamine, allylamine and hydroxylamine, cyclohexylamino (—NHCH(CH$_2$)$_5$), piperidine (—N(CH$_2$)$_5$) and benzylamino (—NHCH$_2$C$_6$H$_5$). Some amines may contain the basic skeletal structure of swainsonine to give analogues such as:

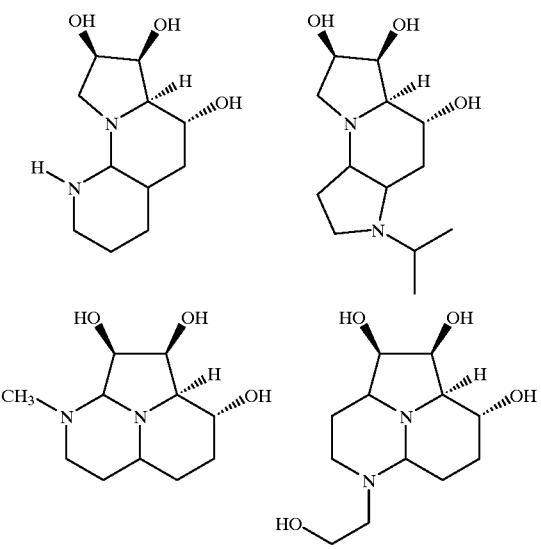

The term "thioalkyl", "thiocycloalkyl", "thioalkynyl", "thiocycloalkenyl", "thiocycloalkynyl", "thiocycloacetylenyl" alone or in combination, refers to a chemical functional group where a sulfur atom (S) is bonded to an alkyl, cycloalkyl, alkenyl, alkynyl, or unsaturated monocyclic hydrocarbon group. The compounds have the general chemical formula —SR$^9$ where R$^9$ is an alkyl, cycloalkyl, alkenyl, alkynyl, or unsaturated monocyclic hydrocarbon group. Examples of thioalkyl groups are thiomethyl, thioethyl, thiopropyl, thiopropenyl, thiobutyl, thiohexyl, thiocyclopentyl, thiomethoxymethyl, thiocyclohexyl, thioallyl, and thiochloromethyl.

The term "thioaryl", alone or in combination, refers to a chemical functional group where a sulfur atom (S) is bonded to an aryl group with the general chemical formula —SR$^{10}$ where R$^{10}$ is an aryl group which may be substituted. Examples of thioaryl groups are thiophenyl, para-chlorothiophenyl, thiobenzyl, 4-methoxy-thiophenyl, 4-nitro-thiophenyl, and para-nitrothiobenzyl.

A "carboxylic acid" chemical functional group, alone or in combination, has the formula —COOH and examples of compounds of the formula I containing one carboxyl group are the following:

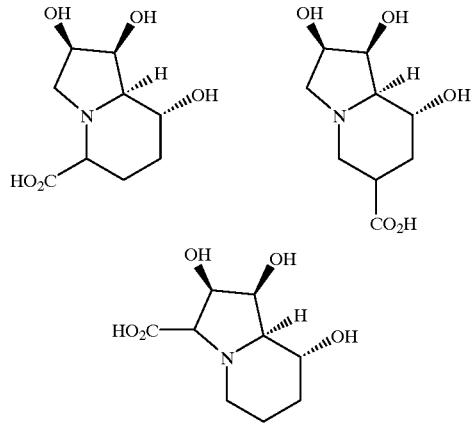

Esters of carboxylic acids have the chemical functional group R$^{11}$COOR$^{12}$ where R$^{11}$ represents the primary skeleton structure of a compound of the formula I and R$^{12}$ is alkyl, cycloalkyl, alkenyl, alkynyl, unsaturated monocyclic hydrocarbons, or aryl. A lactone is a cyclic ester where $R^{11}$ and $R^{12}$ represent the same tether. Preferred carboxylic acid esters (—$CO_2R^{12}$) include methyl esters (—$CO_2CH_3$), ethyl esters (—$CO_2CH_2CH_3$), propyl esters (—$CO_2CH_2CH_2CH_3$), allyl esters (—$CO_2CH_2CH=CH_2$), butyl esters ('$CO_2CH_2CH_2CH_2CH_3$) and benzyl esters (—$CO_2CH_2C_6H_5$). Examples of compounds of the invention bearing only one ester group are the following:

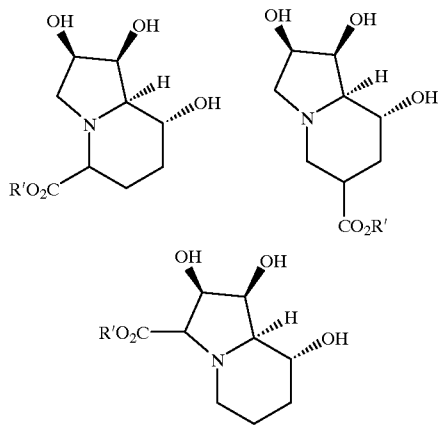

Where, for example R' is $CH_3$, $CH_2CH_3$, $CH_2CH_3CH_3$, $CH_2CH_2CH_2CH_2CH_3$, $CH_2C_6H_5$.

Other examples of esters of compounds of the formula I of the invention include the following:

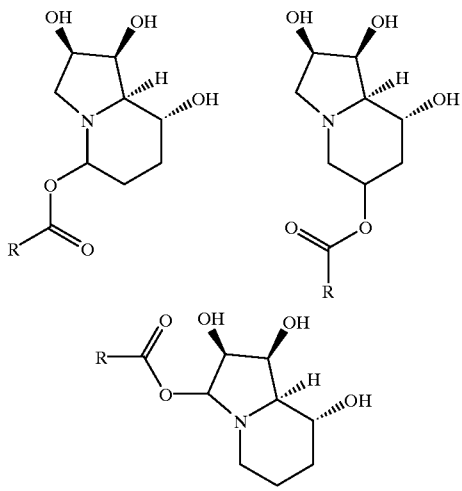

Where, for example, R is methyl, ethyl, propyl, propenyl, butyl, pentyl, hexyl, phenyl or benzyl.

Thioesters have the general formula $R^{13}COSR^{14}$ where $R^{13}$ represents the primary skeleton of a compound of the formula I, and $R^{14}$ is an alkyl, cycloalkyl, alkenyl, alkynyl, unsaturated monocyclic hydrocarbons, or aryl. Examples of thioesters are analogous to those provided for the carboxylic acid esters presented above.

The term "amides", alone or in combination, refers to a chemical functional group of the formula $R^{15}CONR^{16}R^{17}$ where $R^{15}$ represents the primary skeleton of compounds of the formula I, and $R^{16}$, and $R^{17}$ are any combination of hydrogen, alkyl, cycloalkyl, alkenyl, alkynyl, unsaturated monocyclic hydrocarbons, or aryl. Examples of amide substituents for the compounds of the formula I include:

—$CONH_2$, —$CONHCH_3$, —$CON(CH_3)_2$, —$CONHCH_2CH_3$, —$CON(CH_2CH_3)_2$, —$CONHCH_2CH_2CH_3$, —$CONHCH_2CH=CH_2$, —$CONHC_6H_5$, —$CONHCH_2C_6H_5$, —$CONHCH_2CH_2OH$, $CON(CH_2CH_2OH)_2$, —$CON(CH_2CH_2OCH_3)_2$, and

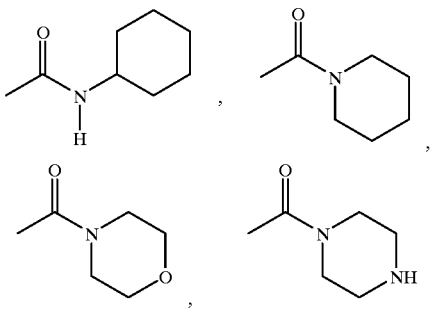

Examples of compounds of the formula I containing an amide substituent include:

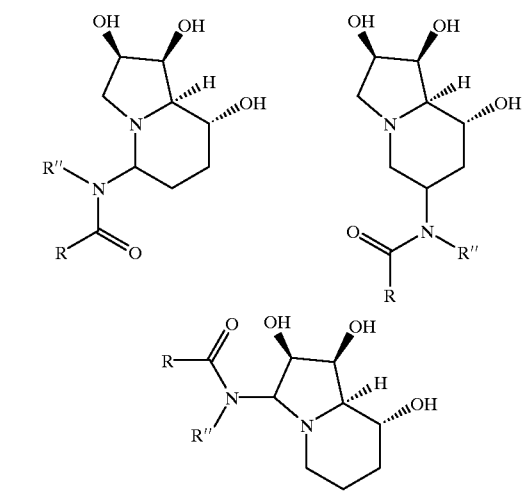

where R and R" are permutations of hydrogen, methyl, ethyl, hydroxyethyl, propyl, hydroxypropyl, butyl, cyclopropyl, cyclobutyl, cyclopentyl, cyclohexyl, phenyl and benzyl for example, or, where R and R" of the basic amide formula may form a lactam ring such as:

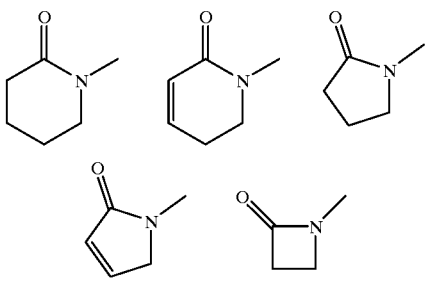

Other lactam rings of interest include structures where both R and R' of the basic amide formula form part of the basic swainsonine skeleton of a compound of the formula I such as:

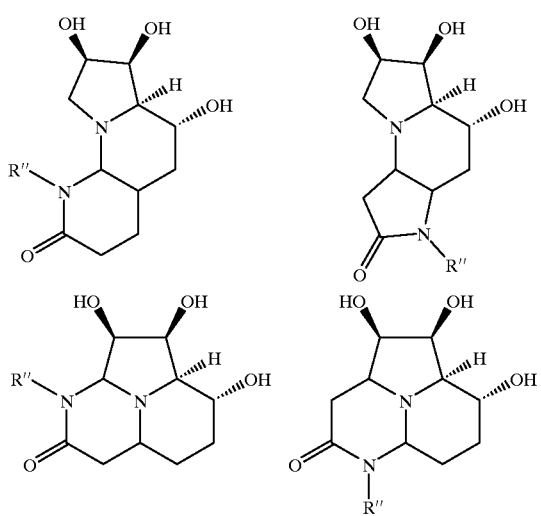

where R'' for example may be hydrogen, methyl, ethyl, hydroxylethyl, propyl, butyl, hexyl or benzyl.

Thioamides have the general formula

where $R^{18}$ represents the primary skeleton of a compound of the formula I, and $R^{19}$ and $R^{20}$ may be any combination of hydrogen, alkyl, cycloalkyl, alkenyl, alkynyl, unsaturated monocyclic hydrocarbons, or aryl. A thiolactam is a cyclic thioamide where $R^{18}$ and $R^{19}$ represent the same tether. Examples of thioamides are analogous to those described for amides above.

Sulfonamides have the general formula

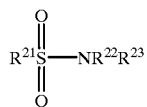

where $R^{21}$ represents the general structure of the compounds of the formula I, $R^{22}$ and $R^{23}$ may be any combination of hydrogen, alkyl, cycloalkyl, alkenyl, alkynyl, unsaturated monocyclic hydrocarbons, or aryl. Examples of thioamides are analogous to those described for amides above.

Hydrazides have the general formula $R^{24}C(O)NR^{25}NR^{26}R^{27}$ where $R^{25}$ represents alkyl, cycloalkyl, alkenyl, alkynyl, unsaturated monocyclic hydrocarbons, or aryl, one of $R^{24}$, $R^{26}$ or $R^{27}$ represents the primary skeleton of a compound of the formula I, and the other of $R^{24}$, $R^{26}$ and $R^{27}$, may be any combination of hydrogen, alkyl, cycloalkyl, alkenyl, alkynyl, unsaturated monocyclic hydrocarbons, or aryl. Examples of hydrazide substituent groups where $R^{24}$ represents the primary skeleton of a compound of the formula I include hydrazide (—C(O)NHNH$_2$), dimethyl hydrazide (—C(O)NHN(CH$_3$)$_2$) or benzyl hydrazide (—C(O)NHNHCH$_2$C$_6$H$_5$). Examples of hydrazide substituent groups where $R^{26}$ or $R^{27}$ represent the primary skeleton of a compound of the formula I include CH$_3$C(O)NHNH—, CH$_3$CH$_2$C(O)NHNH—, CH$_3$CH$_2$CH$_2$CH$_2$C(O)NHNH— or C$_6$H$_5$C(O)NHNH—.

Hydrazines have the general formula

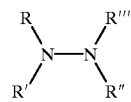

where R, R', R'' and R''' can be any combination of hydrogen, alkyl, cycloalkyl, alkenyl, alkynyl, unsaturated monocyclic hydrocarbons, or aryl. Examples of hydrazine substituents include: —NHNH$_2$, —NHNHCH$_2$C$_6$H$_5$ and —NHN(CH$_3$)$_2$.

Hydrazones have the general formula

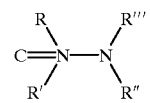

where one of R, R', R'' and R''' represents the primary skeleton of a compound of the formula I, and the other of R, R', R'' and R''' can be any combination of hydrogen, alkyl, cycloalkyl, alkenyl, alkynyl, unsaturated monocyclic hydrocarbons, or aryl. Examples of compounds of the formula I with hydrazone substituents, which may or may not be cyclic and form part of the swainsonine skeleton of a compound of the formula I include the following:

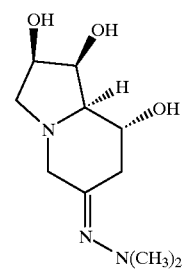

Ureas have the general formula:

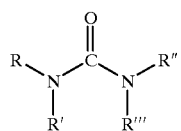

where one of R, R', R" and R'" represents the primary skeleton of a compound of the formula I, and the other of R, R', R" and R'" can be any combination of hydrogen, alkyl, cycloalkyl, alkenyl, alkynyl, unsaturated monocyclic hydrocarbons, or aryl. Examples of urea substituents and urea containing compounds of the formula I include:

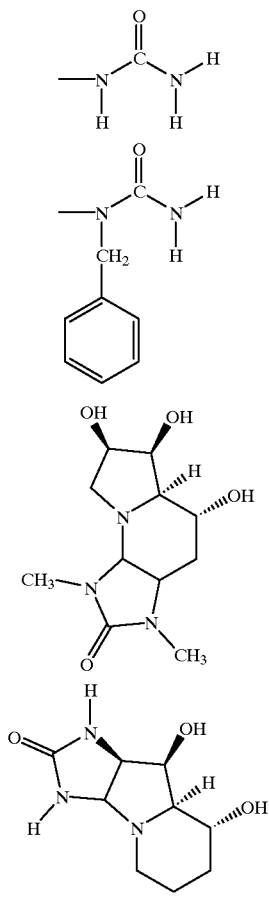

Thioureas have the general formula:

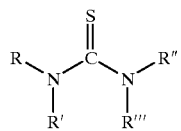

where one of R, R', R" and R'" represents the primary skeleton of a compound of the formula I, and the other of R, R', R" and R'" can be any combination of hydrogen, alkyl, cycloalkyl, alkenyl, alkynyl, unsaturated monocyclic hydrocarbons, or aryl. Examples of thiourea substituents and thiourea containing compounds of the formula I are analogous to those provided above for ureas.

The term "ketones" refers to a chemical functional group of the formula $R^{28}COCR^{29}$, where $R^{28}$ represents the primary skeleton of a compound of the formula I and $R^{29}$ is alkyl, cycloalkyl, alkenyl, alkynyl, unsaturated monocyclic hydrocarbons, or aryl. Examples of ketones which may be used in the compounds of the invention include methyl ketones (—$COCH_3$), methylene methyl ketones (—$CH_2COCH_3$), ethylene methyl ketones (—$CH_2CH_2COCH_3$), ethyl ketones (—$COCH_2CH_3$), propylketones, vinylketones, butylketones (—$COCH_2CH_2CH_2CH_3$), hexylketones, cyclohexylketones, cyclopentylketones, phenylketones and benzylketones. Compounds of the formula I containing cyclic ketone groups include the following:

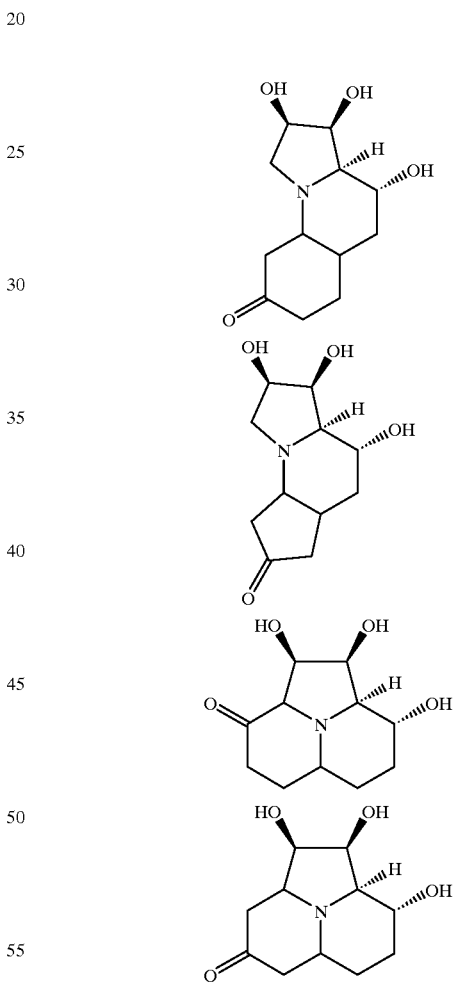

Thioketones have the general formula:

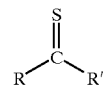

where R represents the primary skeleton of a compound of the formula I and R' is alkyl, cycloalkyl, alkenyl, alkynyl, unsaturated monocyclic hydrocarbons, or aryl. Examples for thioketones are analogous to those given above for ketones.

Carbamates have the general formula:

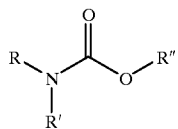

where one of R and R" represents the primary skeleton of a compound of the formula I, and the other of R and R' are hydrogen, alkyl, cycloalkyl, alkenyl, alkynyl, unsaturated monocyclic hydrocarbons, or aryl , and R' is hydrogen alkyl, cycloalkyl, alkenyl, alkynyl, unsaturated monocyclic hydrocarbons, or aryl, or R and R' represent the same compound of the formula I. Examples of carbamate substitutents (—NR'CO$_2$") for compounds of the formula I include O-allyl carbamates (—NHCO$_2$CH$_2$CH=CH$_2$), O-ethyl carbamates (—NHCO$_2$CH$_2$CH$_3$), O-tert-butyl carbamates (—NHCO$_2$C(CH$_3$)$_3$) and O-benzyl carbamates (—NHCO$_2$CH$_2$C$_6$H$_5$). Examples where both R and R" form part of the primary skeleton of a compound of the formula I (i.e. swainsonine) include:

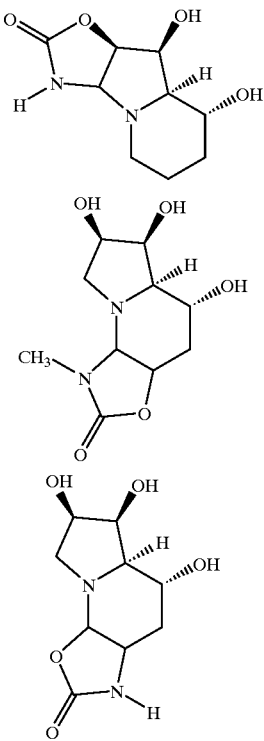

Thiocarbamates have the general formula:

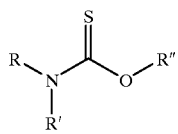

where one of R and R" represents the primary skeleton of a compound of the formula I, and the other of R and R" represents hydrogen, alkyl, cycloalkyl, alkenyl, alkynyl, unsaturated monocyclic hydrocarbons, or aryl and R' is hydrogen, alkyl, cycloalkyl, alkenyl, alkynyl, unsaturated monocyclic hydrocarbons, or aryl. Examples for thiocarbamates are analogous to those given above for carbamates.

Xanthates have the general formula:

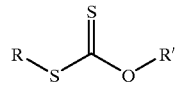

where R and/or R' are the primary structure of a compound of the formula I. Examples of xanthates (—SC(S)OR') where R contains the primary skeleton of a compound of the formula I (i.e. swainsonine) include O-methyl xanthates (—SC(S)OCH$_3$), O-ethyl xanthates (—SC(S)OCH$_2$CH$_3$) or O-benzyl xanthate (—SC(S)OCH$_2$CH$_3$). Examples of xanthates (—OCS$_2$R) where R' contains the primary skeleton of a compound of the formula I (i.e. swainsonine) include S-methyl xanthates (—OCS$_2$CH$_3$), S-ethyl xanthates (—OCS$_2$CH$_2$CH$_3$) or S-benzyl xanthate (—OCS$_2$CH$_2$CH$_3$).

Sulfoxides have the general formula R$^{30}$SOR$^{31}$ where R$^{30}$ and/or R$^{31}$ represent the primary skeleton of a compound of the formula I. Examples of sulfoxides of interest include those where R$^{30}$ represents the primary skeleton of a compound of the formula I (i.e. swainsonine), and R$^{31}$ includes for example, methyl sulfoxides (—SOCH$_3$), methylene methyl sulfoxides (—CH$_2$SOCH$_3$), ethylene methyl sulfoxides, (—CH$_2$CH$_2$SOCH$_3$), ethyl sulfoxides (—SOCH$_2$CH$_3$), butyl sulfoxides (—SOCH$_2$CH$_2$CH$_2$CH$_3$), hexylsulfoxides, cyclohexylsulfoxides, cyclopentylsulfoxides, allyl sulfoxides, phenylsulfoxides and benzylsulfoxides. Other sulfoxides of interest include those where both R$^{30}$ and R$^{31}$ form part of the primary skeleton of a compound of the formula I (i.e. swainsonine) to give cyclic sulfoxides such as:

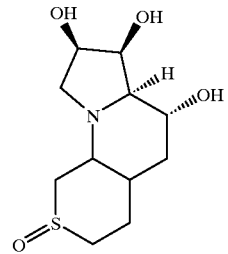

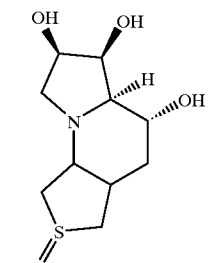

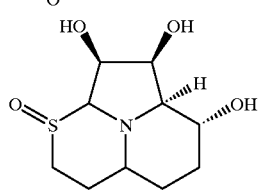

-continued

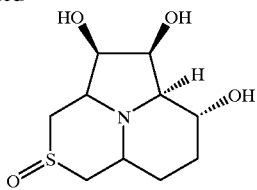

Sulfones have the general formula:

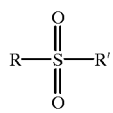

where R and/or R' represent the primary skeleton of a compound of the formula I. Examples of sulfones are analogous to the sulfoxides described above.

Epoxides (or oxiranes) are 3-membered cyclic ethers having the general formula:

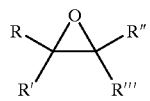

where one of R, R', R" and R'" represents the primary skeleton of a compound of the formula I, and the other of R, R', R" and R'" can be any combination of hydrogen, alkyl, cycloalkyl, alkenyl, alkynyl, unsaturated monocyclic hydrocarbons, or aryl. Some examples of epoxides include:

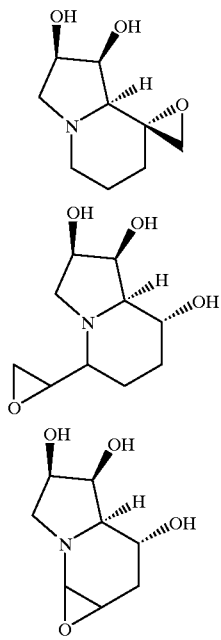

-continued

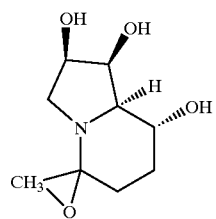

Similarly, 4-, 5- and 6-membered saturated cyclic ethers which may be used in the compounds of the formula I include trimethylene oxide (($CH_2)_3O$), tetrahydrofuran (($CH_2)_4O$), and tetrahydropyran (($CH_2)_5O$) rings.

Ammonium salts have the general formula:

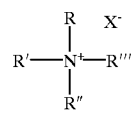

where one of R, R', R" and R'" is a primary skeleton of a compound of the formula I and the other of R, R', R", R'" is hydrogen, alkyl, cycloalkyl, alkenyl, alkynyl, unsaturated monocyclic hydrocarbons, or aryl, and $X^-$ is a suitable counterion such as chloride ($Cl^-$), bromide ($Br^-$) or acetate ($CH_3CO_2^-$). Examples of ammonium salts include trimethylammonium chloride (—$N(CH_3)_3Cl$), methylpiperidylammonium bromide (—$N(CH_3)(CH_2)_5Br$) or benzyldiethyl ammonium chloride (—$N(CH_2C_6H_5)(CH_2CH_3)_2Cl$).

Thiols (also known as mercaptans) have the general formula $R^{37}$—SH where $R^{37}$ is a primary skeleton of a compound of the formula I. Nitro compounds have the general formula $R^{38}$—$NO_2$ where $R^{38}$ is a primary skeleton of a compound of the formula I. Organic azides have the general formula $R^{39}$—$N_3$ where $R^{39}$ is a primary skeleton of a compound of the formula I.

Hydroxylamines have the general formula $R^{40}$—$NR^{41}$(OH), where $R^{40}$ is the primary skeleton of a compound of the formula I and $R^{41}$ is hydrogen, alkyl, cycloalkyl, alkenyl, alkynyl, unsaturated monocyclic hydrocarbons, or aryl. Examples of hydroxylamine substituents (—$NR^{75}(OH)$) include hydroxylamino (—NH(OH)), N-methylhydroxylamine (—$N(OH)CH_3$)), N-ethylhydroxylamine (—$N(OH)CH_2CH_3$)) or N-benzylhydroxylamine (—$N(OH)(CH_2C_6H_5)$).

Alkoxy or aryloxy amines have the general formula $R^{42}$—$NR^{43}(OR^{44})$, where $R^{42}$ is a primary skeleton of a compound of the formula I, $R^{43}$ is hydrogen, alkyl, cycloalkyl, alkenyl, alkynyl, unsaturated monocyclic hydrocarbons, or aryl, and $R^{44}$ is alkyl or aryl. Examples of alkoxy or aryloxy amines substituents (—$NR(OR^{44})$) include methoxylamine (—$NH(OCH_3)$), N-ethyl methoxylamine (—$N(OCH_3)CH_2CH_3$)) or N-benzyl ethoxylamine (—$N(CH_2CH_3)(CH_2C_6H_5)$).

Nitriles have the general formula $R^{45}$—CN where $R^{45}$ is the primary skeleton of a compound of the formula I. Thiocyanates have the general formula $R^{46}$—SCN where $R^{46}$ is the primary skeleton of a compound of the formula I.

Imines (also known as Schiff bases) have the general formula

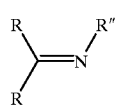

where R is a primary skeleton of a compound of the formula I and, R' and R" can be any combination of hydrogen, alkyl, cycloalkyl, alkenyl, alkynyl, unsaturated monocyclic hydrocarbons, or aryl.

Sulfinic acids have the general formula $R^{47}$—$SO_2H$ where $R^{47}$ is a primary skeleton of a compound of the formula I. Sulfonic acids have the general formula $R^{48}$—$SO_3H$ where $R^{48}$ is a primary skeleton of a compound of the formula I.

Sulfonic acid esters have the general formula:

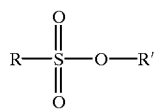

Examples of sulfonic acid esters where R' contains the basic skeleton of a compound of the formula I i.e. the swainsonine skeleton, include tosylates (p-$CH_3C_6H_4SO_3$—) and mesylates ($CH_3SO_3$—). Other examples where R contains the basic skeleton of a compound of the formula I i.e. the swainsonine skeleton, include methyl esters (—$SO_3CH_3$), ethyl esters (—$SO_3CH_2CH_3$) or benzyl esters (—$SO_3CH_2C_6H_5$).

Triazoles have the general formula:

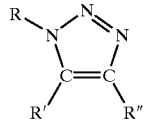

where one of R, R' and R" is a basic skeleton of a compound of the formula I and the other of R, R', and R" can be any combination of hydrogen, alkyl, cycloalkyl, alkenyl, alkynyl, unsaturated monocyclic hydrocarbons, or aryl. Examples of compounds of the invention including triazoles are the following:

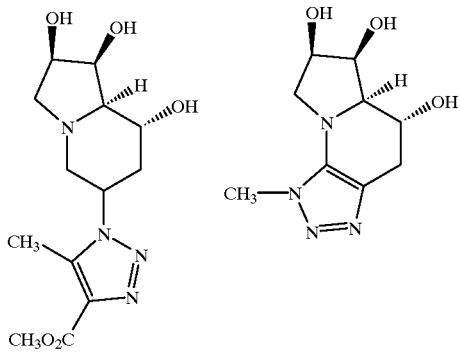

Imides have the general formula:

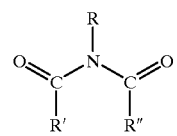

where one of R, R' and R" is a basic skeleton of a compound of the formula I and the other of R, R' and R" can be any combination of hydrogen, alkyl, cycloalkyl, alkenyl, alkynyl, unsaturated monocyclic hydrocarbons, or aryl. Examples of compounds of the formula I where an imide forms part of the skeleton of the compound of the formula I include:

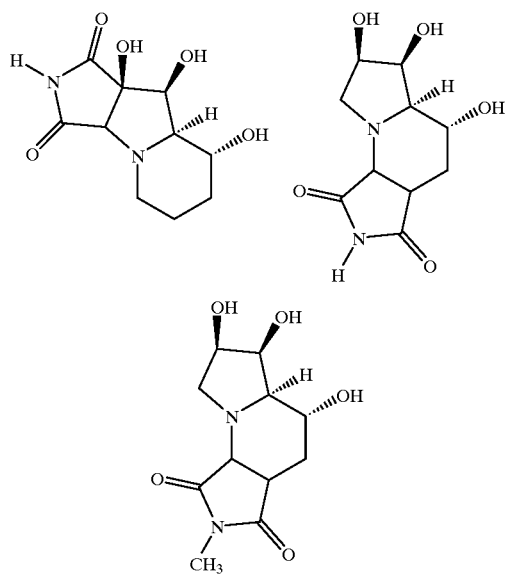

Imidazole rings which may be used in the compounds of the formula I have the general formula:

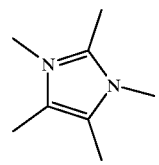

Examples of swainsonine analogues of the invention having an

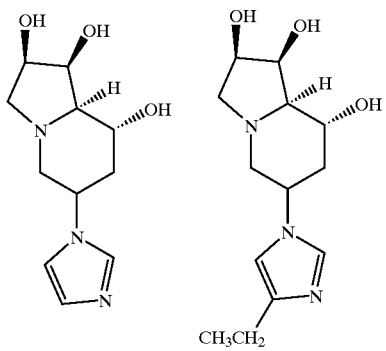

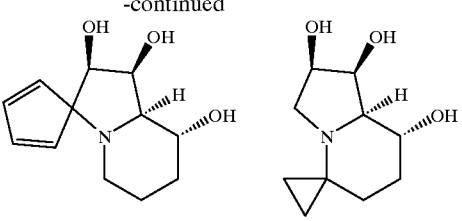

The term "carbocyclic" or "carbocyclic ring system" refers to molecular rings where the framework is constructed by joining carbon atoms solely and includes but is not limited to any stable 3- to 7-membered monocyclic or bicyclic or 7- to 14-membered bicyclic or tricyclic or up to 26-membered polycyclic carbon ring, any of which may be saturated, partially unsaturated, or aromatic. Examples of carbocyclic rings include substituted or unsubstituted cycloalkyl, monocyclic unsaturated hydrocarbons, and aryl as described herein, including but not limited to benzene and napthalene.

Heterocyclic rings are molecular rings where one or more carbon atoms have been replaced by hetero atoms (atoms not being carbon) such as for example, oxygen (O), nitrogen (N) or sulfur (S), or combinations thereof. Examples of heterocyclic rings include ethylene oxide, tetrahydrofuran, thiophene, piperidine (piperidinyl group), pyridine (pyridinyl group), and caprolactam. A carbocyclic or heterocyclic group may be optionally substituted at carbon or nitrogen atoms with for example, alkyl, phenyl, benzyl or thienyl, or a carbon atom in the heterocyclic group together with an oxygen atom may form a carbonyl group, or a heterocyclic group may be fused with a phenyl group.

A spiro ring is defined as two rings originating from the same atom (the spiro center). A spiro ring is schematically represented below:

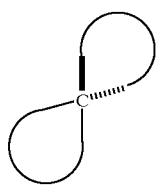

Some examples of swainsonine analogues of the invention containing spiro rings include:

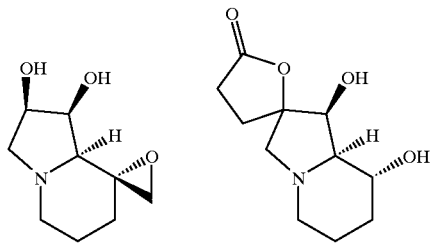

One or more of $R^1$, $R^2$, $R^3$, W, W', W", X, X', Y, Y', Z, and/or Z', alone or together, which contain available functional groups as described herein may be substituted with one or more of the following: alkoxy, hydroxyl, thiol, thiol, —$SR^9$ wherein R9 is alkyl, cycloalkyl, alkenyl, alkynyl, or unsaturated monocyclic hydrocarbons, thioaryl, amino, ammonium, halogen, carboxylic acid or ester, ketone, aldehyde, carbonate, carbamate, amide, azide, imide, imine, imidazole, acetal, ketal, nitrile, diazo, nitro, hydrazine, hydrazide, hydrazone, hydroxamic acid, oxime, hydroxylamine, sulfate, sulfonic or sulfinic acid or ester, sulfonamide, phosphate or phosphonate acids or esters, silyl, sulfoxide, sulfone, oxime, guanidino, phosphonate, thioamide, thiocarbamate, thiocyanate, thioketone, thiourea, triazole, cyano, nitrile, urea or xanthate. The term "one or more" used herein preferably refers to from 1 to 3 substituents, most preferably 1 to 2 substituents. Examples of substituted radicals are described herein, and include but are not limited to —$CH_2R^{50}$ where $R^{50}$ is alkyl, aryl, amino, —$CR^{51}$ where $R^{51}$ is halogen, in particular trifluoromethyl, and —$CH_2OR^{52}$ where $R^{52}$ is alkyl or aryl.

In one embodiment of the invention, compounds of the formula I are provided where W, W' and W" are the same and represent hydroxyl. In another embodiment of the invention, a compound of the formula I is provided wherein $R^1$, $R^2$, and $R^3$ are the same and represent hydrogen. In a still further embodiment of the invention, compounds of the formula I are provided where $R^1$, $R^2$, and $R^3$ are the same and represent hydrogen, and W, W' and W" are the same and represent hydroxyl.

In particular the invention contemplates compounds of the formula I where:

(a) $R^1$, $R^2$, and $R^3$ represent hydrogen, and W, W' and W" represent hydroxyl, and Z and Z' represent hydrogen;

(b) $R^1$, $R^2$, and $R^3$ represent hydrogen, and W, W' and W" represent hydroxyl, and X and X' represent hydrogen;

(c) $R^1$, $R^2$, and $R^3$ represent hydrogen, and W, W' and W" represent hydroxyl, and X, X', Z and Z' represent hydrogen;

(d) $R^1$, $R^2$, and $R^3$ represent hydrogen, and W, W' and W" represent hydroxyl, Y and Y' represent hydrogen;

(e) one of Y and Y' represents methyl, hydroxymethyl, ethyl, phenyl, benzyl, benzyloxymethyl, or fluoromethyl;

(f) one of X and X' represents methyl which may be substituted such as thiomethyl, fluoromethyl, or methoxy;

(g) W" and $R^3$ are the same and represent halogen, preferably fluoro; and (h) Y and Y' are the same and represent halogen, preferably fluoro.

Preferably the compounds of the formula I of the invention are those where:

(a) $R^1$, $R^2$, and $R^3$ represent hydrogen, W, W' and W" represent hydroxyl, Z and Z' represent hydrogen, one of X and X', which may be substituted, is alkyl, aryl, alkoxy, hydroxyl, thiol, thioalkyl, thioaryl, amino, halogen, carboxylic acid esters, thiol esters, benzyl, pyridinyl, —$CH_2OR^{52}$ where $R^{52}$ represents alkyl or aryl, and the other of X and X' is hydrogen, or X and X' together represent =O, and, one of Y and Y', which may be substituted, is alkyl, aryl, alkoxy, hydroxyl, thiol, thioalkyl, thioaryl, amino, halogen, carboxylic acid esters, thiol esters, —$CH_2OR^{52}$ where $R^{52}$ represents alkyl or aryl, benzyl, or and the other of Y and Y' is hydrogen;

(b) $R^1$, $R^2$, and $R^3$ represent hydrogen, W, W' and W" represent hydroxyl, Y and Y' represent hydrogen, X and X', which may be substituted, are the same or different and represent hydrogen, alkyl, aryl, alkoxy, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl, and Z and Z' are the same or different and represent alkyl, aryl, alkoxy, hydroxyl, thiol, thioalkyl, thioaryl, amino, halogen, carboxylic acid esters, thiol esters, benzyl, or pyridinyl, or $CH_2OR^{52}$ where $R^{52}$ represents alkyl or aryl, with the proviso that at least one of X and X' and at least one of Z and Z' cannot be hydrogen;

(c) $R^1$, $R^2$, and $R^3$ represent hydrogen, W, W' and W" represent hydroxyl, X and X' represents hydrogen, Y, Y', Z, and Z' are the same or different and represent hydrogen, alkyl, aryl, alkoxy, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl, which may be substituted, with the proviso that at least one of Y and Y' and at least one of Z and Z' cannot be hydrogen; most preferably one of Y and Y' and one of Z and Z' represents alkyl, aryl, hydroxyl, thiol, thioalkyl, benzyl, pyridinyl , or —$CH_2OR^{50}$ where $R^{50}$ represents alkyl or aryl, which may be substituted, and the other of Y and Y' and Z and Z' represents hydrogen;

(d) $R^1$, $R^2$, and $R^3$ represent hydrogen, W, W' and W" represent hydroxyl, X, X', Z and Z' represent hydrogen, and one of Y and Y', which may be substituted, represent alkyl, aryl, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl, and the other of Y and Y', which may be substituted, represents hydrogen, alkyl, aryl, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl;

(e) $R^1$, $R^2$, and $R^3$ represent hydrogen, W, W' and W" represent hydroxyl, Y, Y', Z and Z' represent hydrogen, one of X and X' represents alkyl, aryl, alkoxy, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl, which may be substituted, and the other of X and X', which may be substituted, represent hydrogen, alkyl, aryl, alkoxy, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl, or X and X' together represent =O;

(f) $R^1$, $R^2$, and $R^3$ represent hydrogen, W, W' and W" represent hydroxyl, Z and Z' represent hydrogen, and X and Y, X' and Y', X' and Y, or X and Y' together form a 6 member heterocyclic ring containing one or two of O, S, or N.

Particularly preferred compounds of the invention are compounds of the formula I where:

1. One of Y and Y' and one of Z and Z' represents alkyl, aryl, alkoxy, hydroxyl, thiol, thioalkyl, benzyl, pyridinyl, or —$CH_2OR^{52}$ where $R^{52}$ represents alkyl or aryl, which may be substituted, and the other of Y and Y' and Z and Z' represents hydrogen.

2. $R^1$, $R^2$, and $R^3$ represent hydrogen, W, W' and W" represent hydroxyl, X, X', Z and Z' represent hydrogen, and one of Y and Y' represents methyl, ethyl, phenyl, or benzyl which may be substituted, preferably trifluoromethyl, hydroxymethyl, and benzyloxymethyl, and the other of Y and Y' represents hydrogen;

3. $R^1$, $R^2$, and $R^3$ represent hydrogen, and W represents hydroxyl, and W' and W" represent halogen, preferably fluoro; X, X', Z and Z' represent hydrogen, and one of Y and Y' represents methyl, ethyl, phenyl, or benzyl, which may be substituted, preferably trifluoromethyl, hydroxymethyl, and benzyloxymethyl and the other of Y and Y' represents hydrogen;

4. one of Y and Y' is hydrogen and the other of Y and Y' is methyl, and one of Z and Z' is hydroxymethyl, —$COCH_2CH_3$, —CN, —$CH_2NH_2$, —$CH_2NHAc$, or —$CH_2NHCR^{60}$=NH where $R^{60}$ is alkyl or aryl;

5. one of Z and Z' is —$CONR^{70}R^{71}$ where $R^{70}$ and $R^{71}$ are the same or different and represent hydrogen, alkyl, or aryl, —COOH, —$COOC_2H_5$, methyl, or $CH_2OH$, or Z and Z' together form a spiro ring; or 6. X and Y form a carbocyclic or heterocyclic ring of the formula $R^{75}$—$R^{76}$—$R^{77}$—$R^{78}$—$R^{79}$ where $R^{75}$ and $R^{79}$ are part of the swainsonine skeleton and one or more of $R^{76}$, $R^{77}$, and $R^{78}$ represent CH, $CH_2$, O, S, or N.

Selected compounds of the formula I are the following: (5R)-5-methylswainsonine, (5R)-5-methylswainsonine formate salt, (5S)-5-methylswainsonine, (5R)-8-Epi-5-methylswainsonine, (5S)-5-ethylswainsonine, (5S,6S)-6-hydroxymethyl-5-methylswainsonine; (5R)-5-benzyloxymethylswainsonine, (5R,6R)-6-hydroxymethyl-5-methylswainsonine,(5R)-5-hydroxymethylswainsonine, (5S)-5-hydroxymethylswainsonine, (5R,6R)-6-hydroxymethyl-5-methyl swainsonine, (5S)-5-benzyloxymethylswainsonine, ethyl (1R, 2R,5S,6S,8S, 8aR)-1,2,8-trihydroxy-5-methyloctahydro-6-indolizinecarboxylate,

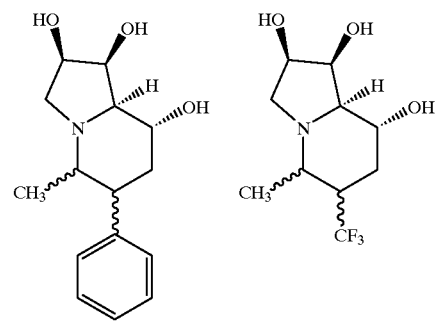

-continued

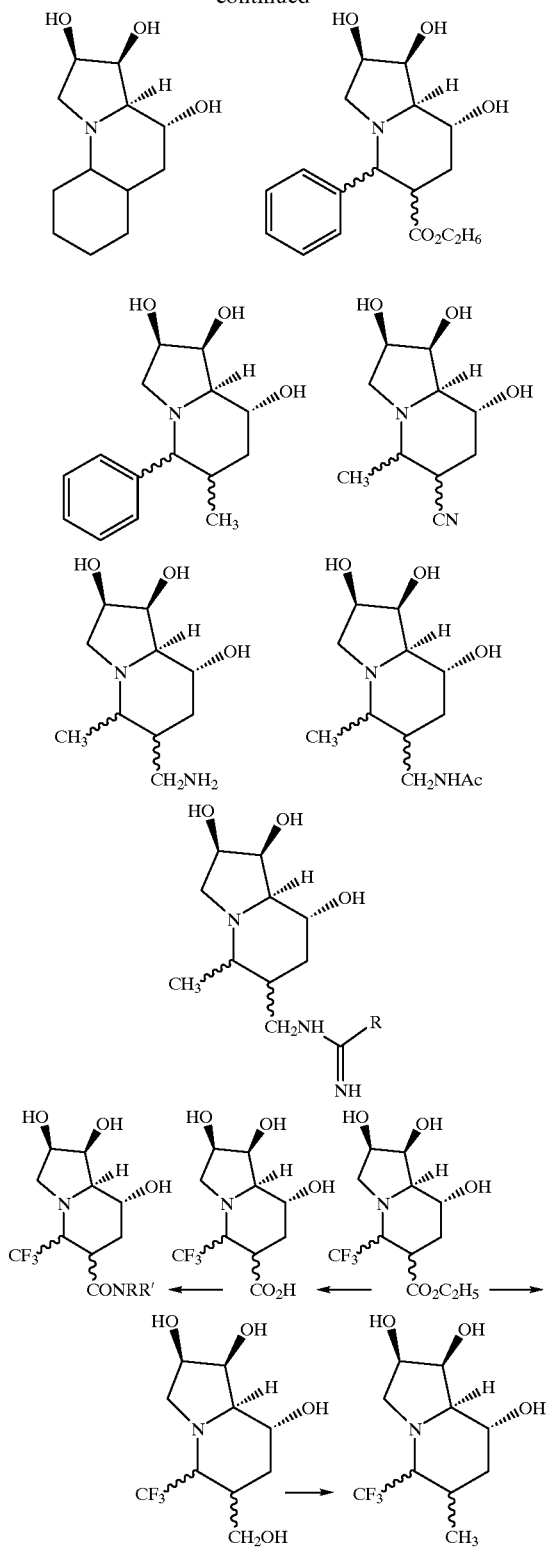

It will be appreciated that, owing to the asymmetrically substituted carbon atoms in formula I, a compound of formula I may exist in, and be isolated in, optically active and racemic forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. It will be appreciated that the (S)-isomer and the (R)-isomer are convertible by facile epimerization of the chiral centers, and that a preparation containing a compound of formula I as a mixture of the (S)- and (R)-isomers of the formula I is within the scope of the invention.

Therefore, the present invention contemplates all optical isomers and racemic forms thereof of the compounds of the invention and the formulas of the compounds shown herein are intended to encompass all possible optical isomers of the compounds so depicted.

The present invention also contemplates salts and esters of the compounds of the formula I of the invention. In particular, the present invention includes pharmaceutically acceptable salts. By pharmaceutically acceptable salts is meant those salts which are suitable for use in contact with the tissues of humans and lower animals without undue toxicity, irritation, allergic response and the like, and are commensurate with a reasonable benefit/risk ratio. Pharmaceutically acceptable salts are well known in the art and are described for example, in S. M. Berge, et al., J. Pharmaceutical Sciences, 1977, 66:1–19. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

II. Processes for Preparing Compounds

The compounds of the formula I of the present invention can be prepared by utilizing procedures and techniques well known and appreciated by one of ordinary skill in the art. By way of illustration, descriptions of some methods that may be used to prepare compounds of the formula I of the invention are set forth herein.

Compounds of the Formula I wherein $R^1$, $R^2$, and $R^3$ represent hydrogen, W, W' and W'' represent hydroxyl, and X, X', Z and Z' represent hydrogen may be synthesized in a variety of ways by adapting common synthetic organic chemistry practices to known synthetic intermediates. For example, as shown in schematic form in FIG. 1, the known (B. P. Bashyal, Tetrahedron, 43(13):3083–3093 (1987)) azido alcohol 2 can be oxidized to provide the corresponding aldehyde which is then reacted (Wittig reaction) with a variety of commercially available or custom synthesized phosphoranes or phosphonate derivatives (3 and 4 respectively) to give α,β-unsaturated ketone of the type 5 where the group X can be any chemical group such as methyl, chloromethyl, trifluoromethyl, ethyl, n-propyl, iso-propyl, cyclopropyl, n-butyl, sec-butyl, tert-butyl, cyclobutyl, pentyl, hexyl, phenyl, benzyl, etc. Catalytic hydrogenation of 5 followed by removal of the isopropylidene protecting group under standard conditions then gives the desired 5-substituted swainsonine derivatives. Further functional group manipulations such as oxidation, reduction, nucleophilic additions or substitutions etc. of the new substituents can further increase the number of derivatives from the limited number of Wittig reagents originally used to construct the core molecule. Alternatively, reduction of the ketone 5 to the corresponding amino alcohols 6 can give mixtures of 5- and 5' substituted swainsonine derivatives after a Mitsunobu style cyclization reaction to close the 6-membered ring, followed by the usual catalytic hydrogenation to cyclize the 5-membered ring, and final isopropylidene removal (FIG. 2). The concept of displacing a leaving group, generated from an alcohol function, with an amine as in 6 in order to cyclize the 6-membered ring of swainsonine can be performed by a variety of strategies that include, for example, protection of the amino group with a benzyloxycarbonyl (CBZ) group followed by mesylation of the free hydroxyl and nucleophilic displacement of the mesyl group by the amine generated during a catalytic hydrogenation step that simultaneously cyclizes both rings into the required compounds of the formula I, and which is apparent to anyone skilled in the art of synthetic organic chemistry.

There are many possible synthetic routes that can be used to prepare 5, 5'-disubstituted swainsonine analogues using some of the concepts described above. For example, reduction of the azido group in 2 followed by protection of the resulting amine with a suitable protecting group such as fluorenylmethoxycarbonyl (Fmoc) gives the alcohol 7. Oxidation followed by a Wittig reaction using phosphoranes or phosphonates as described above gives the ketone 8. Selective reduction of the alkene with palladium oxide and subsequent removal of the amine protecting group using piperidine for example, leads to the formation of a cyclic imine which can be reacted with any nucleophile to provide the 5, 5'-disubstituted swainsonine analogues after final catalytic hydrogenation and isopropylidene removal (FIG. 3B).

Alternatively, substituents at the 5 position of swainsonine can be introduced by reacting the known amide 9 with suitable Wittig reagents. Further modifications such as oxidative hydroboration or simple reduction of the new alkene 10 can also give a number of new 5-substituted derivatives (FIG. 4).

3,5-disubstituted swainsonine analogues i.e. compounds of the Formula I wherein $R^1$, $R^2$, and $R^3$ represent hydrogen, W, W' and W" represent hydroxyl, and Z and Z' represent hydrogen may also be prepared by a variety of methods. For example, temporary protection of the amine 11 with an Fmoc group followed by mild reduction of the anomeric benzyl group under neutral conditions gives the corresponding hemiacetal 12 which then spontaneously temporarily generates a cyclic iminium complex 13 upon deprotection of the amine using a mild base such as piperidine which then quickly reacts with any nucleophile present to give the protected 3,5-disubstituted swainsonine analogue 14. Mild acid treatment then removes the isopropylidene protecting group to give the desired 3,5-disubstituted swainsonine analogues (FIG. 3A).

Synthetic routes for preparing compounds of the formula I wherein $R^1$, $R^2$, and $R^3$ represent hydrogen, W, W' and W" represent hydroxyl, and Z and Z' represent hydrogen; $R^1$, $R^2$, and $R^3$ represent hydrogen, W, W' and W" represent hydroxyl, and X and X' represent hydrogen; and $R^1$, $R^2$, and $R^3$ represent hydrogen, and W, W' and W" represent hydroxyl, and Z and Z' represent hydrogen; $R^1$, $R^2$, and $R^3$ represent hydrogen and W, W' and W" represent hydroxyl, are shown in FIG. 3A; FIGS. 4, 5 and 6; and FIG. 7, respectively.

Reactive groups used for preparing the compounds of the invention, may be blocked using appropriate protective groups. Appropriate blocking and deblocking schemes are known to the skilled artisan (See T. W. Greene, Protective Groups in Organic Synthesis , John Wiley & Sons, New York, 1981). In general, particular protective groups are selected which adequately protect the reactive groups in question during subsequent synthetic steps and which are readily removable under conditions which will not cause degradation of the desired product. By way of example, ethers, acetals, ketals, and esters can be used to protect isolated hydroxyl groups. In particular, suitable protective groups which may be used in the process of the invention include O-benzyl, O-p-methoxybenzyl, O-acetoxy, O-haloacetoxy, O-benzoyloxy, and O-allyl. Removal of the protective groups may be carried out using procedures known in the art. For example, a p-methoxybenzyl group may be removed using ceric ammonium nitrate in acetonitrile and water.

Appropriate methods for replacing a free hydroxyl group by alkoxy, halo, or amino in blocked/deblocked compounds to produce compounds where for example W, W', and/or W' are alkoxy, aryloxy, halo or amino, are well known to the skilled artisan. In particular, a free hydroxyl group may be converted to an alkoxy or aryloxy group by reacting with alkyl or aryl halide in the presence of a base. To replace the free hydroxyl by a halo group, the compound with the free hydroxyl is first reacted with triflic anhydride, mesyl chloride or tosyl chloride, in the presence of a base like pyridine, to block the hydroxyl with a leaving group such as triflate, mesyl, or tosyl, respectively. The blocked hydroxyl is then replaced by O-benzoate, with inversion, by treatment with sodium benzoate in dimethyl formamide (DMF). The O-benzoate is then de-esterified, blocked again by a suitable leaving group like triflate which, on treatment with tetrabutylammonium halide, is replaced, with inversion, by the respective halide, or on treatment with sodium azide is replaced, with inversion, by azido, and subsequently by amino on reduction.

An alkoxy group may be added by dissolving a compound with a free hydroxyl in DMF and adding it to a flask under an inert atmosphere containing a base (e.g. sodium hydride) at low temperature (0° C. to 10° C.). After stirring for a few minutes, benzyl bromide in DMF is added dropwise at low temperature, for example 0° C. to 10° C. The reaction mixture is further stirred at room temperature for 2 to 24 hours. Conventional work-up of the reaction mixture yields the alkoxy (benzyl) compound.

A halo group, for example, fluoro, may be added by dissolving a compound with a free hydroxyl in dichloromethane (DCM) together with a base like pyridine. After cooling at low temperature (−10° C. to −60° C.), an appropriate amount of triflic anhydride, or mesyl chloride, or tosyl chloride is added dropwise. The reaction is allowed to stir at a temperature between 0° C. to 25° C. Conventional work-up of the reaction mixture yields the esterified compound. Treatment of this derivative with sodium benzoate in DMF is carried out immediately, which replaces the leaving group with O-benzoate with inversion. The free hydroxyl is generated by treatment with a base (e.g. sodium methoxide) and then reblocked by a suitable leaving group such as triflate (repeating the above described method). To obtain a fluoro derivative with inversion, the triflate is treated with anhydrous tetraalkylammonium fluorides (preferably tetra n-butyl) or potassium fluoride in a suitable solvent (e.g diethyl ether, tetrahydrofuran or crown ether).

For the introduction of an amino group, the triflate may be treated either with sodium azide or benzyl amine in DMF. The product may be obtained with an azido or benzyl amine group, with inversion, which on reduction with palladium on carbon in a hydrogen atmosphere gives the free amino group.

Appropriate methods for introducing a thiol group in compounds of the formula I (e.g. where W, W', W", X, X', X', Y, Y', Z, and/or Z' are thiol) are well known to the skilled artisan. For example, a thiol group may be added by nucleophilic substitution of an alkyl halide or sulfonyl ester for example using sodium sulfhydride (NaSH) or, by nucleophilic substitution of a halide or sulfonate ester using thioacetic acid to give a thioacetate group which can then be deblocked to a free thiol upon treatment with sodium methoxide in methanol by converting the same to a Bunte salt using thiosulfate ($S_2O_3^{2-}$) and later hydrolyzing the Bunte salt with an acid or, by treating the hydroxyl group with a fluoropyridinium salt and N,N-dimethyl thiocarbamate (Hojo: Yoshino: Mukaiyama Chem. Lett. (1977) 133:437) or, by oxidizing a hydroxyl to a ketone then converting it to a thioketone with Lawson's reagent and reducing to a thiol with sodium borohydride. For a review, see (Wardell, in Patai "The Chemistry of the Thiol Group, pt 1: Wiley: New York, 1974, pp. 179–211).

Methods for introducing a thioalkyl or a thioaryl group in compounds of the formula I (e.g. where W, W', W", X, X', X', Y, Y', Z, and/or Z' are thioalkyl or thioaryl) are well known to the skilled artisan. For example, by nucleophilic substitution of an alkyl halide or sulfonyl ester for example with alkyl or aryl thiolate salts or with alkyl or aryl thiols in the presence of a base such as 1,8-diazabicyclo[5.4.0] undecene (DBU), by alkylating thiols with alkyl or aryl halides or sulfonate esters or, by treating a hydroxyl group with an alkyl or aryl halide in the presence of tetramethyl thiourea followed by sodium hydride (Fujisaka; Fujiwara; Norisue; Kajigaeshi Bull. Chem. Soc. Jpn. 1985, 58:2529) or, by treating an alcohol with tributyl phosphine and an N-(thioaryl)succinimide in benzene (Waters Tetrahedron Lett. 1977, p. 4475 and references cited within). For a review, see Peach, in Patai "The Chemistry of the Thiol Group, pt 1: Wiley: New York, 1974, pp 721–735.

In addition, appropriate methods for replacing a blocked or deblocked hydroxyl group with a hydrogen in compounds of the formula I are well known to the skilled artisan. For example, alkyl halides or sulfonyl esters such as tosylates can be selectively reduced with lithium aluminum hydride or a variety of other metal hydride reducing agents in different solvents such as ether or diglyme. A large list of methods able to achieve this transformation is provided in J. March "Advanced Organic Chemistry. Reactions, Mechanisms and Structure" 4th Edition, 1992, pp 438–446 and references cited therein.

Some alkyl or aryl groups, particularly those which may contain unsaturations or other chemical functional groups such as halo, carboxyl, hydroxyl, alkoxy, azido or amino for example, can be further derivatized by chemical processes such as oxidation, hydroxylation, hydrolysis, nitration, hydroboration, sulfation, amination, amidation, esterification, alkylation, halogenation, epoxidation, carbonylation, haloformylation, reduction, carbon-carbon chain elongation by Grignard or Wittig reactions for example to introduce new or additional functional groups in any final compound. Such transformations can be achieved by anyone skilled in the art of synthetic organic chemistry.

If necessary, the products of the processes described above may be purified by conventional methods such as column chromatography.

Compounds of the formula I with available hydroxyl groups can be converted to epi-isomers by $SN_2$ inversion. For example, the free hydroxyl can be reacted with mesyl chloride and pyridine to give O-mesyl (methyl sulphonyl), which on treatment with sodium benzoate in DMF (dimethyl formamide) produces a compound where the free hydroxyl group is replaced by epi-O-benzoate. Deesterification using NaOMe in methanol results in a compound of the formula I where the free hydroxyl is replaced by epihydroxyl. Similarly, this $SN_2$ inversion method can be used to displace a hydroxyl by an azido group or halo group (F, Cl, I, Br) in their epi-isomers.

The compounds of the formula I described above may be converted into salts using conventional procedures. For example, where one of X, X', Y, Y', Z, and Z' in a compound of the formula I is a carboxylic acid, the compound may be converted into a salt by treating with a molar equivalent of sodium hydroxide or potassium hydroxide. Where one of X, X', Y, Y', Z, and Z' in a compound of the formula I is an amine, the compound of the formula I may be converted into a salt by treating with acetic acid, hydrochloric acid, or formic acid.

Compounds of the formula I with free hydroxyl groups may also be converted into esters using conventional procedures. For example, the compounds of the formula I may be dissolved in DCM and pyridine. After cooling (0° C. to 5° C.) benzoic anhydride or benzoyl chloride in DCM and pyridine is added dropwise. The reaction is allowed to stir at room temperature for 2 to 24 hours. Conventional work-up yields the esterified derivatives.

Optical antipodes of the compounds of the formula I may be prepared from the corresponding racemic forms by standard optical resolution techniques, involving, for example, the separation of diastereomeric salts of those compounds of the formula I characterized by the presence of a basic amino group, and an optically active acid, or by synthesis from optically active precursors.

III. Utility of Compounds of the Invention

The compounds of the formula I are inhibitors of oligosaccharide processing and in particular are inhibitors of mannosidase. General mannosidase inhibition may be tested by measuring the inhibition of Jack Bean, α-mannosidase, and lysosomal α-mannosidase. Mannosidase inhibition may also be tested using an L-PHA toxicity assay. The assay is based on the finding that the specific binding of the toxic plant lectin L-PHA to transformed cell lines such as MDAY-D2 tumor cells is a specific measure of inhibition of oligosaccharide processing. The measurement of $IC_{50}$ in the L-PHA toxicity assay reflects the ability of the compound to enter into cells and to effect inhibition of oligosaccharide processing. It is a general screen for activity in cells which measures cell entry, inhibition of the target enzyme, α-mannosidase II in the Golgi, and the resulting cellular phenotype.

Therefore, a compound of the invention may be tested for its ability to inhibit N-linked oligosaccharide processing by growing transformed cells in the presence of L-PHA and the compound; measuring the amount of proliferation of the cells; and determining the ability of the compound to inhibit N-linked oligosaccharide processing by comparing the amount of proliferation of the cells with the amount of proliferation observed for the cells grown in the presence of L-PHA alone.

Transformed cells which may be used in this assay include MDAY-D2, L1210, CHO, B16, melanoma tumor cells, and human tumor cells such as SW 480, LS174T, HT-29, WiDr, T2, MDA-231, MCF7, BT-20, Hs578T, K562, Hs578T, SK-BR-3, CY 6T, MDA-468, H23, H157, H358, H1334, H1155, H28, H460, Hmesol, H187, H510A, N417, H146, H1092, H82 (Restifo, N. P. et al, J. Exper. Med. 177:265–272, 1993).

The amount of proliferation of the cells may be measured using conventional techniques. For example, cell proliferation may be measured by measuring incorporation of labeled thymidine. More particularly, radioactively labeled thymidine may be added for about 2–5 hours, preferably 3–4 hours and the cells can be harvested and radioactivity counted using a scintillation counter.

The conditions for carrying out the above assay will be selected having regard to the nature of the compound and the cells employed. For example, if the transformed cells are MDAY-D2 tumor cells a concentration of about $1–4 \times 10^4$ cells, preferably $2 \times 10^4$ may be used. The MDAY-D2 cells are generally cultured for about 10 to 30 hours, preferably 18 to 20 hours, followed by addition of L-PHA at a concentration of about 10–50 $\mu$g/ml, preferably 20–30 $\mu$/ml, most preferably 25 $\mu$g/ml.

The following L-PHA assay may be used to assay for inhibition of oligosaccharide processing (i.e. Golgi $\alpha$-mannosidase II) in viable cells. MDAY-D2 tumor cells are inoculated into 96 well micro-test plates at $2 \times 10^4$ cells/well, containing serial dilutions of the compound to be tested in MEM plus 10% FCS. The cells are cultured for 18–20 hours, followed by the addition of L-PHA at 25 $\mu$g/ml for an additional 24 hours. Cell proliferation is measured by adding 0.5 $\mu$Ci/well of $^3$H-thymidine for 3–4 hours, harvesting onto glass fibre disks using a Titertek harvester, and counting the disks in a liquid scintillation counter. The apparent $IC_{50}$ values for the test compounds are the drug concentrations showing 50% protection from L-PHA toxicity; that is 50% $^3$H-thymidine incorporated compared with cells grown in the absence of L-PHA.

The ability of the compounds of the formulae I in which the free hydroxyls have been esterified, to be converted into more active compounds in cells can be measured by performing the L-PHA toxicity assay in the presence of an esterase inhibitor such as diethyl p-nitrophenyl phosphate. For example, the esterase inhibitor diethyl p-nitrophenyl phosphate can be added to MDAY-D2 cells in the above described assay method about 4 hours prior to the $\alpha$-mannosidase inhibitors. An increase in $IC_{50}$ in the L-PHA toxicity assay in the presence of diethyl p-nitrophenyl phosphate indicates that the compound requires activation by esterases and would accordingly be useful as a prodrug. This method may be used to screen for prodrugs and can be used to identify substances which inhibit all steps in the N-linked oligosaccharide pathway prior to β1-4 Gal-transferase.

The compounds of the formula I have valuable pharmacological properties and they provide immunostimulatory, antimicrobial and cancer suppressing effects. In particular, the compounds are useful in the prevention, treatment and prophylaxis of tumor growth and metastasis of tumors. The anti-metastatic effects of the compounds of the invention may be demonstrated using a lung colonization assay. For example, melanoma cells treated with a compound may be injected into mice and the ability of the melanoma cells to colonize the lungs of the mice may be examined by counting tumor nodules on the lung after death. Suppression of tumor growth in mice by the compound administered orally or intravenously may be examined by measuring tumor volume.

The compounds of the formula I have particular application in the prevention of tumor recurrence after surgery i.e. as an adjuvant therapy.

The compounds of the invention are especially useful in the treatment of various forms of neoplasia such as leukemias, lymphomas, melanomas, adenomas, sarcomas, and carcinomas of solid tissues in patients. In particular the composition may be useful for treating malignant melanoma, pancreatic cancer, cervico-uterine cancer, cancer of the kidney, stomach, lung, rectum, breast, bowel, gastric, liver, thyroid, neck, cervix, salivary gland, leg, tongue, lip, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS). The compounds may also be used for other anti-proliferative conditions such as arthrosclerosis and viral infections, in particular AIDS.

The compounds of the formula I may be used to stimulate bone marrow cell proliferation, and they may be used as hemorestorative agents, in particular following chemotherapy or radiotherapy. The myeloproliferative activity of a compound of the formula I may be determined by injecting the compound into mice, sacrificing the mice, removing bone marrow cells and measuring the ability of the compound to stimulate bone marrow proliferation by directly counting bone marrow cells and by measuring clonogenic progenitor cells in methylcellulose assays.

The compounds of the invention are immune modulators and in particular they have immunostimulatory properties. Therefore, the compounds of the formula I may be used in cases where a patient has been immunocompromised such as patients infected with HIV, or other viruses or infectious agents including bacteria and fungi, in patients undergoing bone marrow transplants, and in patients with chemical or tumor-induced immune suppression.

The compounds also have an antiviral effect in particular on membrane enveloped viruses such as retroviruses, influenza viruses, cytomegaloviruses and herpes viruses. The compounds of the invention may also be used in the treatment of inflammation.

The following compounds of the invention show significant inhibition of Golgi $\alpha$-mannosidase II activity over lysosomal mannosidase activity:

(a) Compounds of the formula I wherein $R^1$, $R^2$, and $R^3$ represent hydrogen, W, W' and W" represent hydroxyl, Y, Y', Z and Z' represent hydrogen, and one of X and X' represents methyl, phenyl, or benzyl which may be substituted, preferably fluoromethyl or hydroxymethyl, and the other of X and X' represent hydrogen;

(b) Compounds of the formula I wherein $R^1$, $R^2$, and $R^3$ represent hydrogen, W, W' and W" represent hydroxyl, X, X', Z and Z' represent hydrogen, and one of Y and Y' represents methyl, ethyl, phenyl, or benzyl which may be substituted, preferably trifluoromethyl, hydroxymethyl, and benzyloxymethyl, and the other of Y and Y' represents hydrogen; and (c) Compounds of the formula I wherein $R^1$, $R^2$, and $R^3$ represent hydrogen, W, W' and W" represent hydroxyl, and Y and Y' represent hydrogen, X and X' are the same or different and represent hydrogen, alkyl, aryl, alkoxy, hydroxyl, thiol, thioalkyl, thioaryl, amino, halogen, carboxylic acid esters, thiol esters, benzyl, or pyridinyl, or —$CH_2OR^{52}$ where $R^{52}$ represents alkyl or aryl, which may be substituted, and Z and Z' are the same or different and represent alkyl, aryl, alkoxy, hydroxyl, thiol, thioalkyl, thioaryl, amino, halogen, carboxylic acid esters, thiol esters, benzyl, or pyridinyl, or $CH_2OR^{52}$ where $R^{52}$ represents alkyl or aryl, with the proviso that at least one of X and X' and at least one of Z and Z' cannot be hydrogen.

Particularly preferred compounds are (5S)-5-(hydroxymethyl)swainsonine, (5S)-5-methylswainsonine, (5S)-5-ethylswainsonine, (5R)-5-methylswainsonine, (5S)-5-benzyloxymethylswainsonine, (5R)-5-benzyloxymethylswainsonine, or (5R)-5 -(hydroxymethyl) swainsonine. These compounds are particularly well suited for incorporation into pharmaceutical compositions for use in treating the conditions mentioned herein since they have improved pharmacological properties and selectivity avoid the clinical side effects which can be exhibited by swainsonine.

The term "patient" refers to a warm-blooded animal such as a mammal which is afflicted with a particular disease state or condition as described herein. Examples of animals within the scope of the meaning of the term are dogs, cats, rats, mice, horses, bovine cattle, sheep, and humans.

The compounds of the formula I may be converted using customary methods into pharmaceutical compositions. The pharmaceutical compositions contain the compounds either alone or together with other active substances. Such pharmaceutical compositions can be for oral, topical, rectal, parenteral, local, inhalant, or intracerebral use. They are therefore in solid or semisolid form, for example pills, tablets, creams, gelatin capsules, capsules, suppositories, soft gelatin capsules, liposomes (see for example, U.S. Pat. No. 5,376,452), gels, membranes, and tubelets. For parenteral and intracerebral uses, those forms for intramuscular or subcutaneous administration can be used, or forms for infusion or intravenous or intracerebral injection can be used, and can therefore be prepared as solutions of the compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., U.S.A. 1985). On this basis, the pharmaceutical compositions include, albeit not exclusively, the compounds in association with one or more pharmaceutically acceptable vehicles or diluents, and contained in buffered solutions with a suitable pH and iso-osmotic with the physiological fluids.

The compounds are indicated as therapeutic agents either alone or in conjunction with other therapeutic agents or other forms of treatment (e.g. chemotherapy or radiotherapy). For example, the compounds may be used in combination with anti-proliferative agents, antimicrobial agents, immunostimulatory agents, or anti-inflammatories. In particular, the compounds may be used in combination with anti-viral and/or anti-proliferative agents such as interferons. The compounds of the invention may be administered concurrently, separately, or sequentially with other therapeutic agents or therapies.

In general, a dosage range of the compounds in the composition is envisaged for administration in human medicine of from about 0.001 to 50 mg/kg of body weight daily. In the case of intravenous compositions, the dosage is for example about 0.1 to 0.6 mg/kg/day, and for oral compositions the dosage is about 0.5 to 6 mg/kg/day.

Amounts of drug administered to produce serum levels 10–1000× the $IC_{50}$ for inhibition of oligosaccharide processing in the L-PHA assay are preferably employed.

It will also be appreciated that it may be necessary to deviate from the amounts mentioned and in particular to do so as a function of the body weight of the animal to be treated, the particular disease to be treated, the nature of the administration route and the therapy desired. In addition, the type of animal and its individual behavior towards the medicine or the nature of its formulation and the time or interval at which it is administered may also indicate use of amounts different from those mentioned. Thus it may suffice, in some cases, to manage with less than the above-mentioned minimum amounts whilst in other cases the upper limit mentioned must be exceeded. Where major amounts are administered, it may be advisable to divide these into several administrations over the course of the day.

The following non-limiting examples are illustrative of the present invention:

EXAMPLES

Example 1

Synthesis of 5-Substituted Swainsonine Analogues

A. Synthesis of (5S)-5-Methylswainsonine(GD28) and 5{R)-5-Methylswainsonine(GD20)

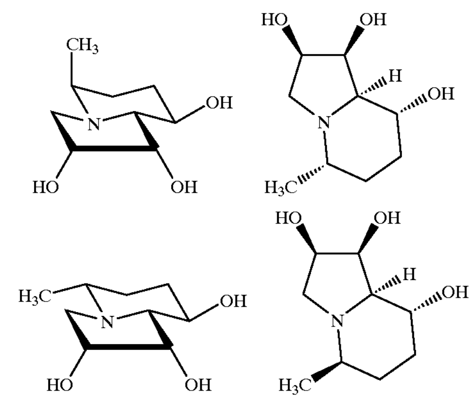

Benzyl 4-azido-4,6,7,9-tetradeoxy-2,3-O-isopropylidene-α-D-manno-nona-6-enopyranoside-8-ulose (GDLZ1)

Pyrdinium chlorochromate (776 mg, 3.6 mmol) was added to a vigorously stirred suspension of flame-dried 3 Å molecule sieves (3 g ) and benzyl 4-azido-2,3-O-isopropylidene-α-D-mannopyranoside (500 mg, 1.49 mmol) in anhydrous methylene chloride (50 mL). After 30 min the oxidation was complete, the slurry was loaded on top of a silica gel column (50 g) and the product eluted with 1:1 ethyl acetate:hexanes. Aldehyde-containing eluent was concentrated, the residue dissolved in anhydrous benzene (30 mL), the solution cooled to 0° C., and triphenylphosphoranylidene-2-propanone (1.2 g, 3.77 mmol) in anhydrous tetrahydrofuran (30 mL) added. The solution was stirred at room temperature overnight. The reaction mixture was concentrated to dryness, the residue chromatographed (16 g silica gel, 1:3 ethyl acetate:hexanes), and gave GDLZ1 (340 mg, 61%) as a spontaneously crystallizing syrup.

Benzyl 4-azido-4,6,7,9-tetradeoxy-2,3-O-isopropylidene-D/L-glycero-D-manno-α-nona-6-enopyranoside (GDLZ18)

Sodium borohydride (150 mg) was added to a stirred solution of crude GDLZ17 (1.46 g, ~3.91 mmol) in 1:1 methylene chloride:methanol. After 30 min the reaction was complete, the solution was concentrated to dryness, the residue chromatographed (34 g silica gel, 1:2 ethyl acetate:hexanes), and gave GDLZ18 (1.38 g, 94%).

Benzyl 4-(N-benzyloxycarbonyl)amino-4,6,7,9-tetradeoxy-2,3-O-isopropylidene-D/L-glycero-D-manno-α-nonapyranoside (GDLZ21)

A suspension of GDLZ21 (550 mg, 1.47 mmol) and 10% palladium on charcoal (50 mg) in 95% ethanol was stirred under hydrogen of atmospheric pressure overnight. The catalyst was filtered off, sodium hydrogencarbonate (0.5 g) was added, and to the stirred suspension benzyl chloroformate (0.5 mL) was added in portions over a period of 2 h. The mixture was filtered, the filtrate concentrated, and chromatographed (2:3 ethyl acetate:hexanes). The product (649 mg, 90%) was obtained as a slowly crystallizing syrup.

Benzyl 4-(N-benzyloxycarbonyl)amino-4,6,7,9-tetradeoxy-2,3-O-isopropylidene-8-O-tosyl-D/L-glycero-D-manno-α-nonapyranoside (GDLZ22)

4-Toluenesulfonyl chloride (140 mg, 0.73 mmol) was added to a solution of GDLZ21 (43 mg, 88 μmol) in anhydrous pyridine and left stirring overnight. The solution was cooled to 0° C. and excess reagent hydrolyzed with water (1 mL). The solution was transferred into water (50 mL) and the product extracted with ethyl acetate (4×10 mL). The combined extracts were neutralized with NaHCO₃ solution, washed with water, dried, and concentrated. The residues was purified by column chromatography (10 g silica gel, 2:3 ethyl acetate:hexanes) and gave GDLZ22 (49 mg, 87%) as a colourless syrup.

Benzyl 4,6,7,8,9-pentadeoxy-4,8-(N-benzyloxycarbonyl)amino-2,3-O-isopropylidene-L-and -D-glycero-D-manno-α-nonapyranoside (GDLZ29A and GDLZ29B)

Solid potassium tert.-butoxide (100 mg) was added to a stirred solution of GDLZ22 (380 mg, 594 μmol) in anhydrous tetrahydrofuran (20 mL). Overnight the reaction was complete. The suspension was concentrated, the residue transferred into water (50 mL) and the products extracted with ethyl acetate (4×20 mL). The combined extracts were washed with water, dried, and concentrated. The isomeric mixture was resolved and the isomers purified by column chromatography (18 g silica gel, 1:4 ethyl acetate:hexanes). The faster migrating isomer (GDLZ29A, 78.5 mg, 28%), the slower migrating isomer (GDLZ29B, 87.2 mg, 31%), and unresolved mixture (47.3 mg, 17%) were obtained as colourless syrups.

(5S)-1,2-O-Isopropylidene-5-methylswainsonine (GDLZ27)

Palladium on charcoal (10%, 80 mg) was added to a solution of compound GDLZ29A (84 mg, 180 mmol) in 95% ethanol (6 mL), and the suspension stirred under hydrogen of atmosphere pressure. After 1.5 h the starting material was consumed, indicating that the first step of reduction (removal of the benzylcarbamate) was complete. The suspension was then acidified by addition of 1M hydrochloric acid (180 μl) and further hydrogenolized overnight. Ion-exchange resin (Dowex 1×8 100, OH⁻-form, 1 g) was added, stirred for 5 min, and filtered off together with the catalyst. The filtrate was concentrated and gave the crude acetonide (38 mg, ~92%).

(5S)-5-Methylswainsonine (GD 28)

Compound GDLZ27 (25 mg, 110 mmol) was dissolved in aqueous 70% trifluoroacetic acid (3 mL) and stirred at room temperature overnight. The solution was concentrated to dryness, the residue dissolved in water (0.5 mL), and the free base generated by addition of a strongly basic ion-exchange resin (BioRad, AG 1-X8 20–50 mesh, OH⁻-form). The solution was removed from the resin, and the resin extracted with water (5×0.5 mL). The extracts were pooled, filtered and freeze-dried. The product was obtained as a white solid (13.0 mg, 63%).

(5R)-1,2-O-Isopropylidene-5-methylswainsonine (GDLZ34)

Palladium on charcoal (10%, 37 mg) was added to a solution of compound GDLZ29B (210 mg, 0.45 mmol) in 95% ethanol (14 mL), and the suspension stirred under hydrogen of atmosphere pressure. After 3 h the starting material was consumed. The suspension was acidified by addition of 1M hydrochloric acid (450 ml) and further hydrogenolized for 3 days. Ion-exchange resin (Dowex 1×8 100, OH⁻-form, 3 g) was added and stirred for 5 min. The suspension was filtered and the filtrate concentrated to give the crude acetonide (136 mg, quantitative).

(5R)-5-Methylswainsonine formate salt (GD19)

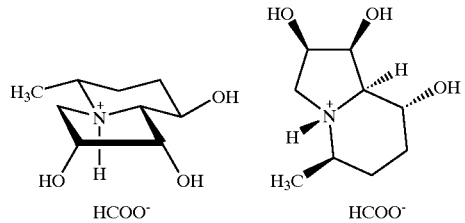

(5R)-1,2-O-Isopropylidene-5-methylswainsonine (63 mg, 0.28 mmol) was dissolved in 50% aqueous trifluoroacetic acid and the solution stirred at room temperature for three days. The solution was concentrated, and the residue purified by reversed phase HPLC using a 20 mM ammonium formate buffer (pH 3.5). Product-containing fractions were freeze-dried several times to remove all traces of buffer and yielded (SR)-5-methylswainsonine as the formate salt (GD19).

(5R)-5-Methylswainsonine (GD20).

An aqueous solution of GD19 was eluted through a column of freshly regenerated basic ion-exchange resin (DOWEX 1×8-100, 50–100 mesh, hydroxyl form). Eluent containing the free base (GD20) was combined and concentrated.

B. Synthesis of (5S)-5-Ethylswainsonine

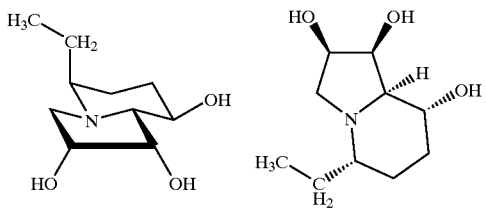

1-Bromo-2-butanol (GDLZ103)

Carbontetrabromide (26.6 g, 80 mmol) and triphenylphosphine (21 g, 80 mmol) were added successively to 1,2-butanediol (7.2 g, 80 mmol) in anhydrous pyridine at 0° C., and the solution stirred at room temperature overnight. The mixture was concentrated and the residual oil dropwise added to vigorously stirred 1:5 ethyl acetate:hexanes (220 mL). The solution was decanted from the precipitate, concentrated, chromatographed (40 g silica gel, 1:3 ethyl acetate:hexanes), and gave GDLZ103 (11.5 g, 90%).

2-Butanonyltriphenylphosphonium bromide (GDLZ105)

Pyridinium chlorochromate (20 g, 93 mmol) was added to a suspension of flame-dried 3 Å molecular sieves (15 g) and GDLZ103 (11.5 g, 75 mmol) in anhydrous methylene chloride, and the mixture stirred for 1 h., the brown slurry was loaded on top of a silica gel column (40 g), and the product eluted using 1:5 ethyl acetate:hexanes. The ketone-containing eluates were combined, concentrated, and the residue reacted with triphenylphosphine (12 g, 46 mmol) in chloroform (20 mL). The solution formed overnight was added slowly into stirred diethyl ether (300 mL) and the precipitate filtered off. The residue was recrystallized from methylene chloride (50 mL) by addition of hexanes. GDLZ105 (3.539 g, 11.4%) was obtained as colourless crystals.

Triphenylphosphoranylidene-2-butanone (GDLZ113)

Finely powdered GDLZ105 (2.5 g, 6.05 mmol) was added to aqueous 10% sodium carbonate solution (150 mL), and stirred vigously overnight. The solid formed was filtered off, thoroughly washed with water, and dried in vacuo in a desiccator overnight. GDLZ113 (1.9 g, 94%) was obtained as an electrostatic, off-white powder.

Benzyl 4-azido-4,6,7,9,10-pentadeoxy-2,3-O-isopropylidene-α-D-manno-dec-6-enopyranoside-8-ulose (GDLZ102)

A slurry of flame-dried 3 Å molecule sieves (1 g), benzyl 4-azido-2,3-O-isopropylidene-α-D-mannopyranoside (133 mg, 0.40 mmol), and pyridinium chlorochromate (0.8 g, 3.71 mmol) in anhydrous methylene chloride (40 mL) was vigorously stirred for 30 min. The mixture was loaded on top of a silica gel column (16 g) and the product eluted using 1:1 ethyl acetate:hexanes. The eluent was concentrated, the residue dissolved in 1:1 anhydrous benzene-tetrahydrofuran (10 mL), and GDLZ113 (180 mg, 0.541 mmol) added. After stirring overnight the mixture was concentrated, the residue chromatographed (12 g silica gel, 1:5 ethyl acetate:hexanes), and gave GDLZ102 (95 mg, 61%) as a slightly yellow syrup.

Benzyl-4-azido-4,6,7,9,10-pentadeoxy-2,3-O-isopropylidene-D/L-glycero-D-manno-α-dec-6-enopyranoside (GDLZ115)

Sodium borohydride (55 mg, 1.45 mmol) was add to a solution of GDLZ102 (800 mg, 2.06 mmol) in methanol (25 mL), and the mixture stirred for 30 min. The solution was concentrated to dryness, the residue chromatographed (1:5→1:2 ethyl acetate:hexanes), and gave GDLZ115 (560 mg, 70%) as a colourless syrup.

Benzyl-4-(N-benzyloxycarbonyl)amino-4,6,7,9,10-pentadeoxy-2,3-O-isopropylidene-D/L-glycero-D-manno-α-decopyranoside (GDLZ116)

10% Palladium on charcoal (~100 mg) was added to a solution of GDLZ115 (560 mg, 1.44 mmol) in ethanol (25 mL), and the mixture stirred under hydrogen of atmospheric pressure overnight. The catalyst was filtered off, sodium hydrogencarbonate (0.5 g) was added, and the mixture stirred while benzyl chloroformate (500 µL) was added in portions via a syringe over a period of 1 h. The suspension was then filtered, the filtrate concentrated, and the residue chromatographed (1:2 ethyl acetate:hexanes). GDLZ116 (500 mg, 69.5%) was obtained as a colourless foam.

Benzyl-4-(N-benzyloxycarbonyl)amino-4,6,7,9,10-pentadeoxy-2,3-O-isopropylidene-8-O-tosyl-D/L-glycero-D-manno-α-decopyranoside (GDLZ117)

A solution of GDLZ116 (500 mg, 1.02 mmol) and 4-toluenesulfonyl chloride (430 mg, 2.3 mmol) in anhydrous pyridine (25 mL) was stirred at room temperature overnight. Excess reagent was hydrolysed by addition of water (1 mL). The solution was transferred into water (300 mL), and the product extracted using ethyl acetate (4×50 mL). The combined extracts were washed with 1M hydrochloric acid, neutralised with aqueous sodium bicarbonate solution, washed with water, dried and concentrated. The residue was chromatographed (1:2 ethyl acetate:hexanes) and gave GDLZ117 (586 mg, 89%) as a colourless syrup.

Benzyl-4,6,7,8,9,10-hexadeoxy-4,8-(N-benzyloxycarbonyl) imino-2,3-O-isopropylidene-L- and -D-glycero-D-manno-α-D-decopyranoside (GDLZ118A and GDLZ118B)

A solution of GDLZ117 (586 mg, 0.91 mmol) and potassium tert.-butoxide (110 mg, 0.98 mmol) in anhydrous tetrahydrofuran was stirred at room temperature overnight. The solution was concentrated and the residue chromatographed (1:4→1:2 ethyl acetate:hexanes). The products were rechromatographed, and the fast migrating isomer (GDLZ118A, 130.2 mg, 30%), as well as the slow migrating isomer (GDLZ118B, 139 mg, 32%) were obtained as colourless syrups.

(5S)-5-Ethyl-1,2-O-isopropylideneswainsonine (GDLZ119)

10% Palladium on charcoal (~45 mg) was added to a solution of GDLZ118A (139 mg, 288 µmol) in 95% ethanol and the mixture stirred under hydrogen of atmospheric pressure overnight. Tlc showed complete turnover of the carbamate. The mixture was acidified by addition of 1 M hydrochloric acid (250 µL) and further hydrogenolysed. Overnight a new product was formed (tlc). The catalyst was filtered off and the filtrate eluted through a column of basic ion-exchange resin (8 mL, AG 1x8 20–50 mesh, OH⁻-form). The eluate containing GDLZ119 was concentrated and the residue purified by HPLC (50% MeOH-50% aqueous 20 mM ammonium formate pH 9.0, 7 mL/min, Waters ODS 25×100 mm, uv detection 206 nm). The product was obtained as a formate salt (7 mg, 8.5%).

(5S)-5-Ethylswainsonine (GD 38)

A solution of GDLZ119 (7 mg, 29 µmol) in 1:1 tetrahydrofuran:6 M hydrochloric acid (1 mL) was stirred overnight. The solution was concentrated, the residue taken up in water (1 mL) and eluted through a column of basic ion-exchange resin (10 mL, OH⁻-form). The eluate containing the free base was freeze-dried and gave GDLZ125 (2.8 mg, 48%) as a colourless foam.

C. Synthesis of (5R)- and (5S)-5-(Hydroxymethyl) swainsonine

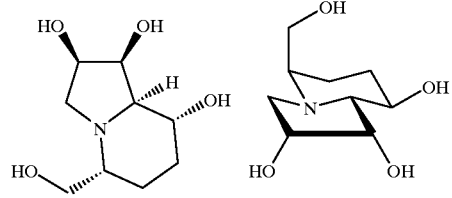
(5R)-5-Hydroxymethylswainsonine

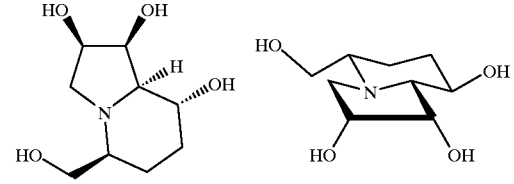
(5S)-5-Hydroxymethylswainsonine

3-Benzyloxy-1-bromo-2-propanol (GDLZ132)

Triphenylphosphine (6.82 g, 26 mmol) and carbontetrabromide (8.63 g, 26 mmol) were added to a solution of 3-benzyloxy-1,2-propanediol (4.72 g, 25.9 mmol) in anhydrous pyridine at 0° C., and stirred overnight at room temperature. The solution was concentrated and the residue dropwise added to vigorously stirred 1:5 ethyl acetate:hexanes (200 mL) to precipitate triphenylphosphineoxide. The supernatant was decanted, concentrated, and the residue chromatographed (60 g silica gel, 1:3 ethyl acetate:hexanes). The product was obtained as a colourless oil (5.1 g, 80%).

3-Benzyloxyacetonyl triphenylphosphoniumbromide (GDLZ135)

Pyridunium chlorochromate (8.5 g, 39.4 mmol) was added to a slurry of compound GDLZ132 (5.1 g, 20.8 mmol) and freshly flame-dried 3 Å molecule sieves (9 g) in anhydrous methylene chloride, and the suspension stirred under argon at room temperature. The reaction was complete after 1 h. The brown slurry was directly loaded on top of a silica gel column (50 g) and the product eluted using 1:2 ethyl acetate:hexanes. Product-containing eluent was concentrated. The residue was diluted with chloroform (10 mL) and reacted with triphenylphosphine (5.5 g) overnight at room temperature. The thick solution obtained was dropwise diluted into vigorously stirred diethyl ether (200 mL), and compound GDLZ135 precipitated as an off-white solid. The product was filtered by suction and dried in vacuo overnight. The product (7.68 g, 73%) was further reacted without purification.

3-Benzyloxy-1-triphenylphosphoranylidene-2-propanone (GDLZ138)

Finely powdered compound GDLZ135 (1.0 g, 1.98 mmol) was added to an aqueous 10% solution of sodium carbonate (30 mL) and the mixture vigorously stirred at room temperature. Overnight, the starting material dissolved and the product precipitated. The suspension was filtered by suction and the off-white residue thoroughly washed with water. The residue was then dried in vacuo over Drierite. The product (817 mg, 97%) was used for the next reaction without any further purification.

Benzyl 4-azido-9-O-benzyl-4,6,7-trideoxy-2,3-O-isopropylidene-α-D-manno-nona-6-enopyranoside-8-ulose (GDLZ150)

A suspension of flame-dried 3 Å molecular sieves (2 g), pyridinium chlorochromate (1.5 g, 6.96 mmol), and benzyl 4-azido-2,3-O-isopropylidene-α-D-mannopyranoside (466 mg, 1.39 mmol) was stirred at room temperature for 30 min. The brown mixture was then loaded on top of a silican gel column (18 g, 1:2 ethyl acetate:hexanes) and the aldehyde eluted. Product-containing fractions were combined and concentrated. The residue was dissolved in anhydrous benzene (20 mL), ylide GDLZ138 (1.0 g, 2.3 mmol) was added, and the mixture stirred at room temperature overnight. The suspension formed was concentrated, the residue chromatographed (35 g silica gel, 1:3 ethyl acetate:hexanes), and gave GDLZ150 (500 mg, 75%) as a colourless syrup.

Benzyl 4-N-(benzyloxycarbonyl)amino-9-O-benzyl-4,6,7-trideoxy-2,3-O-isopropylidene-D/L-glycero-D-manno-α-nonapyranoside (GDLZ166)

A solution of GDLZ150 (834 mg, 1.74 mmol) and sodium borohydride (66 mg, 1.74 mmol) in methanol (20 mL) was stirred at room temperature for 2 h. The solvent was evaporated and the residue chromatographed (33 g silica gel, 1:3 ethyl acetate:hexanes). The reduced glycoside (554 mg, 66%) was then dissolved in 95% ethanol (20 mL), 10% palladium on charcoal (~50 mg) was added, and the solution basicified with two drops of triethylamine. The mixture was then stirred under hydrogen of atmospheric pressure for 3 h. The catalyst was filtered off, sodium hydrogencarbonate (400 mg) was added to the filtrate and stirred while benzyl chloroformate (250 μL, 1.75 mmol) was added in portions over a period of 2 h. Solids were filtered off, the filtrate concentrated and the residue chromatographed (1:1 EtOAc-hexanes). GDLZ166 (557 mg, 54.8% from GDLZ150) was obtained as a colourless syrup.

Benzyl 4-N-(benzyloxycarbonyl)amino-9-O-benzyl-4,6,7-trideoxy-2,3-O-isopropylidene-8-O-tosyl-D/L-glycero-D-manno-α-nonapyranoside (GDLZ169)

4-Toluenesulfonyl chloride (500 mg, 2.6 mmol) was added to a solution of GDLZ166 (557 mg, 953 μmol) in anhydrous pyridine (15 mL) and the mixture stirred at room temperature overnight. Excess reagent was hydrolysed by addition of water (1 mL), and the solution was transferred into water (200 mL). The product was extracted using ethyl acetate (3×50 mL), the combined extracts were washed with 1 M hydrochloric acid, neutralised with sat. aqueous NaHCO$_3$, washed with water, dried, and concentrated. The crude product was chromatographed (30 g silica gel, 1:3→1:2 ethyl acetate:hexanes) and gave pure GDLZ169 (574 mg, 80.8%).

Benzyl 9-O-benzyl-4,6,7,8-tetradeoxy-4,8-(N-benzyloxycarbonyl)imino-2,3-O-isopropylidene-L- and -D-glycero-D-manno-α-nonapyranoside (GDLZ170A and GDLZ170B)

Potassium tert.-butoxide (90 mg, 802 μmol) was added to a solution of GDLZ169 (574 mg, 770 μmol) in anhydrous tetrahydrofuran (25 mL), and the mixture stirred at room temperature under argon overnight. The suspension was transferred into ethyl acetate (100 mL), washed with water and brine, dried, and concentrated. The isomeric mixture was purified by column chromatography (33 g silica gel, 1:3→1:2 ethyl acetate:hexanes), and the diastereomers resolved using preparative HPLC (22:78 ethyl acetate:hexanes, 8 mL/min, 25×100 mm Waters Silica). The faster migrating isomer GDLZ170A (141.5 mg, 32%) and the slower migrating isomer GDLZ170B (157.6 mg, 35.7%) were isolated as colourless syrups.

(5R)-5-Hydroxymethyl-1,2-O-isopropylideneswainsonine (GDLZ162)

Compound GDLZ170A (38 mg, 66 μmol) was hydrogenated in 95% ethanol using 10% palladium on charcoal (~30 mg) and hydrogen of atmospheric pressure under neutral conditions for the removal of the carboxybenzyl group. Overnight the reaction was complete, the mixture was acidified with 1 M hydrochloric acid (80 μL) and further stirred under hydrogen for 3 days. The suspension was filtered, the filtrate concentrated, and the product isolated and purified by HPLC (30:70 0.1% NH$_3$ in MeOH-0.1% NH$_3$ in water, 2 mL/min, 10×150 mm Beckman Ultrasphere ODS). GDLZ162 (7.5 mg, 46.7%) was obtained as a colourless syrup.

(5S)-5-Hydroxymethyl-1,2-O-isopropylideneswainsonine (GDLZ167)

Compound GDLZ170b (57.6 mg, 100 μmol) was hydrogenated in 95% ethanol using 10% palladium on charcoal (~100 mg) and hydrogen of atmospheric pressure. The carboxybenzyl group was removed overnight. The mixture was acidified with 1 M hydrochloric acid (150 μL) and further stirred under hydrogen for 2 days. The suspension was filtered, the filtrate concentrated, and the product isolated and purified by HPLC (30+70 0.1 % NH$_3$ IN MeOH-0.1% NH$_3$ in water, 2 mL/min, 10×150 mm Beckman Ultrasphere ODS). GDLZ167 (9.0 mg, 37% was obtained as a colourless syrup.

(5R)-5-(Hydroxymethyl)swainsonine (GDLZ168/GD45)

A solution of GDLZ162 (7.1 mg, 29.2 μmol) in 2:1 tetrahydrofuran:6 M hydrochloric acid (1.5 mL) was stirred at room temperature overnight. The solution was concentrated, the residue dissolved in water (1 mL), and passed through a column of basic ion-exchange resin to generate the free base. The crude product was purified by HPLC (3:97 0.1% NH$_3$ in MeOH-0.1% NH$_3$ in water, 2 mL/min, 10×150 mm Beckman Ultrasphere ODS) and gave pure GDLZ168 (3.7 mg, 62.3%).

(5S)-5-(Hydroxymethyl)swainsonine (GD 46)

A solution of GDLZ167 (9.0 mg, 37 μmol) in 1:1 tetrahydrofuran:6 M hydrochloric acid (2 mL) was stirred at room temperature overnight. The solution was concentrated, the residue dissolved in 1:1 MeOH:water (2 mL), basicified using basic ion-exchange resin, and passed through a C-18 Sep-Pak-column (Waters). The crude product was purified by HPLC (7:93 0.1 % $NH_3$ in MeOH-0.1% $NH_3$ in water, 2 mL/min, 10×150 mm Beckmann Ultrasphere ODS) and gave GDLZ172 (5.7 mg, 75.8%).

Example 2
Synthesis of 5,6-Disubstituted Swainsonine Analogues

Benzyl-4-amino-4-deoxy-2,3-O-isopropylidene-α-D-mannopyranoside (1)

To a stirred, cooled (ice bath at 0° C.) solution of benzyl-4-azido-4-deoxy-2,3-O-isopropylidene-α-D-mannopyranoside (1.0 g, 3.0 mmol) in dry THF (10 mL) was added $LiAlH_4$ (140 mg, 3.8 mmol) in small portions. The reaction was then allowed to warm to room temperature slowly. After four hours, TLC indicated complete consumption of the starting material and formation of a single new product. The reaction was quenched with 5% $NH_4Cl$ (10 mL) and then worked-up by liquid-liquid extraction ($H_2O$/$CH_2Cl_2$). Upon drying ($MgSO_4$) and concentrating the combined organic extracts, the desired amine 1 was obtained as a white crystalline solid (0.90 g, 2.9 mmol) in 97% yield.

Benzyl-4-benzyloxycarbonylamino-4-deoxy-2,3-O-isopropylidene-α-D-mannopyranoside (2)

To a stirred, cooled (ice bath at 0° C.) solution of 1 (215 mg, 0.70 mmol) in (1:1) THF:10% $NaHCO_3$ (15 mL) was added benzylchloroformate (0.11 mL, 0.75 mmol) dropwise. The reaction was then allowed to warm to room temperature slowly. After stirring for three hours, TLC indicated complete consumption of the starting material and formation of a single new product. Most of the THF was removed by rotary evaporation and $CH_2Cl_2$ and water were added to the remaining aqueous mixture. Following liquid-liquid extraction ($H_2O$/$CH_2CL_2$), the combined organic extracts were dried ($MgSO_4$) and concentrated to give 2 (306 mg, 0.69 mmol) in 97% yield as a white solid. The structure of this product was confirmed by $^1$H-NMR.

Benzyl-4-benzyloxycarbonylamino-4-deoxy-2,3-O-isopropylidene-α-D-mannodialdopyranoside (3)

To a solution of DMSO (0.75 mL, 10.6 mmol) in dry $CH_2Cl_2$ (10 mL) at –50° C. was added oxallylchloride (0.93 mL, 10.6 mmol) dropwise. Stirring was continued for 15 minutes. During that time the cooling bath temperature had risen to –20° C. The solution was cooled to –50° C. before the dropwise addition of a solution of 2 (1.51 g, 3.4 mmol) in dry $CH_2Cl_2$ (15 mL). Stirring was continued at low temperature (–20° C. to –50° C.) for one hour before the addition of triethylamine (9 mL). The reaction was allowed to warm to room temperature and stirring was continued for a further 15 minutes. Water was then added, followed by liquid-liquid extraction ($H_2O$/$CH_2Cl_2$). The combined organic extracts were dried ($MgSO_4$) and concentrated to give the crude aldehyde. This product, which looked relatively clean by TLC, was used in the next step without purification.

Knoevenagel Product (4)

To a cooled (5° C.), stirred solution of ethylacetoacetate (0.9 mL, 7.1 mmol) in dry $CH_2Cl_2$ (20 mL), containing 3≈powdered molecular sieves (1 g), was added a 1 M solution of $TiCl_4$ in $CH_2Cl_2$ (7 mL, 7 mmol). Upon addition of $TiCl_4$ the solution turned yellow then slowly turned orange in colour. To this solution was added pyridine (6 mL, 74 mmol) dropwise which resulted in a colour change to brick red. A solution of 3 in $CH_2Cl_2$ (20 mL) was then added dropwise with continued stirring. Stirring was continued for a further 48 hours. The reaction was then worked up by the addition of aqueous $NaHCO_3$ (10 mL) followed by suction filtration through a glass fiber filter to remove a brown pasty solid. The filtrate was extracted several times with $CH_2Cl_2$. The combined organic extracts were then dried ($MgSO_4$) and concentrated to give a yellow-brown oil. Purification by chromatography (20–30% ethyl acetate in hexanes) gave the desired product (570 mg) as a mixture of cis and trans isomers. The structure of this product was confirmed by $^1$H-NMR.

(5R, 6R) and (5S, 6S) 6-carboethoxy-5-methylswainsonine acetonide (5)

To a solution of 4 (570 mg, 1.03 mmol) in 40 mL ethanol (95%) was added 10% Pd/C (50% wet) (712 mg). This mixture was stirred under $H_2$ (balloon) for two days. At that time TLC showed complete consumption of the starting material. The Pd/C was then filtered off using a glass fiber filter and fresh catalyst was added to the solution. HCl (1M, 1.1 mL, 1.1 mmol) was added and the mixture stirred under $H_2$ (balloon) for a further four days. This reaction gives a mixture of components which include the desired product (70:30 mixture of (5R, 6R) and (5S, 6S) isomers) as the major components. The structure and the ratio of these isomers was inferred by $^1$H-NMR.

Ethyl (1R,2R,5S,6S,8S,8aR)(5S,6S)-1,2,8-trihydroxy-5-methyloctahydro-6-indolizine carboxylate[6-carboethoxy-5-methylswainsonine (GD0036)]

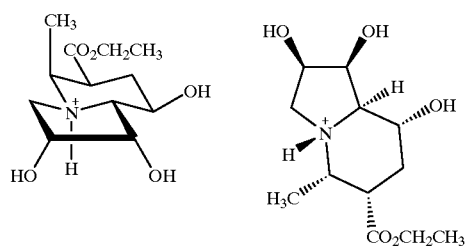

Isolation of (GD0036) was achieved by de-acetonation of the isomeric mixture 5, derivatization of the resulting triols (6) as the TMS ethers, purification of 7 by preparatory GC, followed by acidic hydrolysis of the TMS groups. This isomer (GD0036), which gave an $^1$H-NMR consistent with the structure, was submitted for enzyme assay.

(5R,6R)-6-hydroxymethyl-5-methylswainsonine acetonide and (5S,6S)-6-hydroxymethyl-5-methylswainsonine acetonide (8)

To a solution of isomers 5 (64 mg, 021 mmol) in dry THF was added 20 mg of $LiAlH_4$ in small portions. This suspension was stirred overnight. At that time the starting material had been completely consumed as inferred by TLC. Methanol (1 mL) was added to quench the excess $LiAlH_4$ and stirring was continued for 30 minutes. Celite (0.5 g) was added to this mixture and the methanol was removed by rotary evaporation. The dry Celite/product was then charged onto a $SiO_2$ gel column. Elution with 27:2:1 EtOAc-:MeOH:10% $NH_4OH$ gave the purified isomers along with mixed fractions which were re-chromatographed. The total recovery of (5R,6R) 8 from all fractions was 12 mg. The total recovery of (5S,6S) 8 from all fractions was 15 mg. The structure of these products was confirmed by $^1$H-NMR.

(5S,6S), and (5R,6R)-6-hydroxymethyl-5-methylswainsonine

GD 40
(5S,6S)-6-Hydroxymethyl-5-methylswainsonine

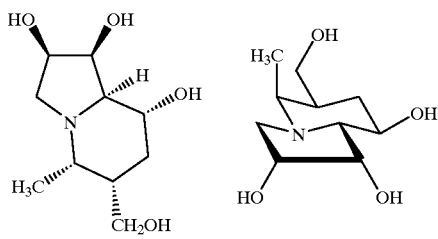

GD 44
(5R,6R)-6-Hydroxymethyl-5-methylswainsonine

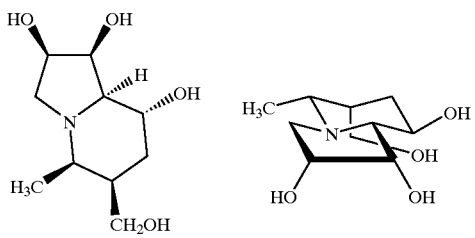

A solution of the acetonide 8 (approx. 5 mg) in THF-6M HCl (2 mL) was stirred at room temperature for two days. The solutions were then concentrated and passed through a hydroxide ion exchange resin column using methanol as an eluent. The free base was then purified using HPLC. Recovery of each isomer was approximately 2–3 mg. These samples, (5S,6S) 6-hydroxymethyl-5-methylswainsonine (GD0040), and (5R,6R)-6-hydroxymethyl-5-methylswainsonine (GD0044) were submitted for enzyme assay.

Example 3
(5R)-5-Benzyloxymethylswainsonine (GD42)

GD 42
(5R)-5-Benzyloxymethylswainsonine

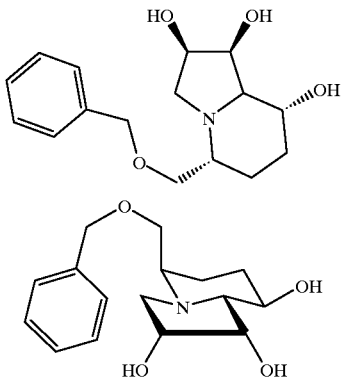

(5R)-5-Benzyloxymethyl-1,2-O-isopropylideneswainsonine (GDLZ177)

Sodium hydride (10 mg, 60% in mineral oil) was added in portions to a stirred solution of crude (5R)-5-hydroxymethyl-1,2-O-isopropylideneswainsonine (30.7 mg, <0.126 mmol) in anhydrous DMF containing benzyl chloride (200 ml). After stirring for two days methanol (1 ml) was added, and the solution concentrated. The residue was purified by reversed phase HPLC and gave GDLZ177 (7.0 mg, ~17%).

(5R)-5-Benzyloxymethylswainsonine (GD42)

Compound GDLZ177 (7.0 mg, 21 mmol) was dissolved in tetrahydrofuran (1 ml), 6 M hydrochloric acid (1 ml) was added, and the solution stirred at room temperature for two days. The solution was concentrated to dryness, the residue purified by reversed phase HPLC, and gave GD42 (2.3 mg, 38%) as a colourless residue.

(5S)-5-Benzyloxymethyl-1,2-O-isopropylideneswainsonine (GDLZ252)

Sodium hydride (7 mg, 60% in mineral oil) was added in portions to a stirred solution of (5S)-5-hydroxymethyl-1,2-O-isopropylidene swainsonine (20.5 mg, 85 mmol) in anhydrous DMF containing benzyl chloride (100 ml). After stirring for two days methanol (1 ml) was added, and the solution concentrated. The residue was purified by reversed phase HPLC and gave GDLZ252 (10.4 mg, 36%).

(5S)-5-Benzyloxymethylswainsonine (GD91)

GC 91
(5S)-5-Benzylozymethylswainsonine

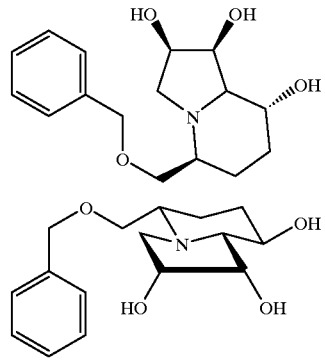

Compound GDLZ252 (6.0 mg, 18 mmol) was dissolved in tetrahydrofuran (1 ml), 6 M hydrochloric acid (1 ml) was added, and the solution stirred at room temperature for two days. The solution was concentrated to dryness, the residue purified by reversed phase HPLC, and gave GD91 (4.9 mg, 93%) amorphous material.

Example 4
(1S, 2S, 3R/S, 8R, 8aS)-3-cyano-1,2,8-Trihydroxyoctahydroindolizine (GD 92)

GD 92

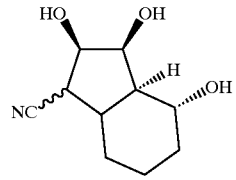

A process for preparing 3-cyano swainsonine is outlined and shown schematically below.
(1R, 3S, 4S, 5S, 6R)-7-Aza-3-benzyloxy-4,5-O-isopropylidenedioxy-2-oxa-biscyclo[4,4,0]-decane (GDSC1009)

To a solution of benzyl E-4-azido-4,6,7-trideoxy-6-ene-2,3-O-isopropylidene-α-D-manno-octadialdopyeanoside (GDSC1005) (1.6g, 4.46 mmol) in ethanol (25 mL) was added 10% palladium on carbon (800 mg, 50% wet). The reaction mixture was stirred under a hydrogen atmosphere overnight. The catalyst was removed by filtration and the solvent was removed under a reduced pressure. The residue was purified by silica gel chromatography (1 to 10% methanol in dichloromethane gradient) to give GDSC1009 1.24 g (3.97 mmol) in 87.6% yield.

(1R, 3S, 4S, 5S, 6R)-7-[N-(tert-Butyloxycarbonyl)amino]-3-benzyloxy-4,5-O-isopropylidenedioxy-2-oxa-biscyclo[4,4,0]-decane (GDSC1117)

To a solution of (1R, 3S, 4S, 5S, 6R)-7-Aza-3-benzyloxy-4,5-O-isopropylidenedioxy-2-oxa-biscyclo[4,4,0]-decane (GDSC1009) (1.40 g, 4.41 mmol) in dioxane/water(1:1, 20 mL) was added 1 N NaOH (10 mL). Di-tert-butyl dicarbonate (2.89 g, 13.23 mmol) was added to this solution and the mixture was stirred at room temperature for 4 h. The reaction mixture was partitioned between dichloromethane (50 mL) and water (60 mL). The organic payer was washed with saturated NaCl (50 ml), dried over MgSO₄ and filtered. The filtrate was evaporated to dryness under reduced pressure and the residue was purified by column chromatography using 0–2% methanol in dichloromethane gradient as eluent to give GDSC1117 (1.38 g, 74.9%).

(1R, 3S, 4S, 5S, 6R)-7-[N-(tert-Butyloxycarbonyl)amino]-3-hyroxy-4,5-O-isopropylidenedioxy-2-oxa-biscyclo[4,4,0]-decane (GDSC1127)

To a solution of (1R, 3S, 4S, 5S, 6R)-7-[N-(tert-Butyloxycarbonyl)amino]-3-benzyloxy-4,5-O-isopropylidenedioxy-2-oxa-biscyclo[4,4,0]-decane (GDSC1117) (1.2 g, 2.86 mmol) in ethanol (50 mL) was added 10% palladium on carbon (1.2g, 50% wet) and a catalytic amount of acetic acid. The flask was evacuated by aspiration and purged with hydrogen three times. The resulting heterogeneous mixture was stirred under a balloon of hydrogen for 8 h. The catalyst was removed by filtration and the solvent was removed under reduced pressure. The residue was then subjected to column chromatography on silica gel, eluting with a gradient of 1–5% methanol in chloromethane to afford GDSC1127 0.810 g (2.46 mmol) in 86% yield as an α,β anomeric mixture. A minor product of this reaction was purified and identified as the deacetonated product of GDSC1127 (ca. 6%).

Synthesis of GDSC1147

A solution GDSC1127 (0.5 g, 1.52 mmol) in DMSO (3 mL) and acetic anhydride (3 mL) was stirred at room temperature under argon for 14 h., the solution was diluted with dichloromethane (25 mL), then poured into a saturated NaHCO₃ solution (25 mL). The organic layer was dried (Na₂SO₄), filtered and concentrated under reduced pressure. The residue was purified by column chromatography using 1% methanol in dichloromethane as eluent to give GDSC1147 (0.457 g) in 92% yield.

Synthesis of GDSC1149

GDSC1147 (215 mg, 0.657 mmol) was dissolved in 0.5 ml of dichloromethane. To this solution was added 4 mL of 80% TFA in water. The reaction mixture was stirred at room temperature for 12 h. The reaction mixture was concentrated under reduced pressure and coevaporated twice with water (10 mL). After being evaporated under high vacuum overnight, the residue was dissolved in 5 mL of 0.2 N sodium methoxide and stirred at room temperature under argon for 20 h. The reaction mixture was concentrated on a rotary evaporator. The orange residue was dissolved in a minimum amount of water and subjected to sequential purifications using Dowex 50WXx2-200 (H⁺) and an AG 1-X8 (OH⁻) ion exchange resins followed by a C-18 column purification to give GDSC1149 (96 mg, 78%) as a crystalline compound.

Synthesis of 3-cyano swainsonine (GDSC3027)

GDSC1 147 (110 mg, 0.334 mmol) was dissolved in a mixture of 0.3 mL of dichloromethane, 3.2 mL of TFA and 0.8 mL of water. The reaction mixture was stirred at room temperature for 12 h. The reaction mixture was concentrated on a rotary evaporator. The residue was dissolved in water (4 mL) and stirred with AG 1-X8 (OH⁻) ion exchange resin (0.5 g dry resin). After 30 min, the mixture was filtered and the filtrate was concentrated. The residue was dissolved in methanol (4 mL) and stirred with potassium cyanide (217 mg, 3.34 mmol) for 12 h. The mixture was concentrated. The residue was dissolved in 1 mL of water and filtered through an AG 1-X8 OH⁻ ion exchange resin column (1.0 g), rinsing with water (12 mL). The filtrate was concentrated and residue was purified with a C-18 column (1 g) using 10–50% methanol in water as eluents to give GDSC3027 (56 mg) as 1:1 α,β mixture of 3-cyano swainsonine.

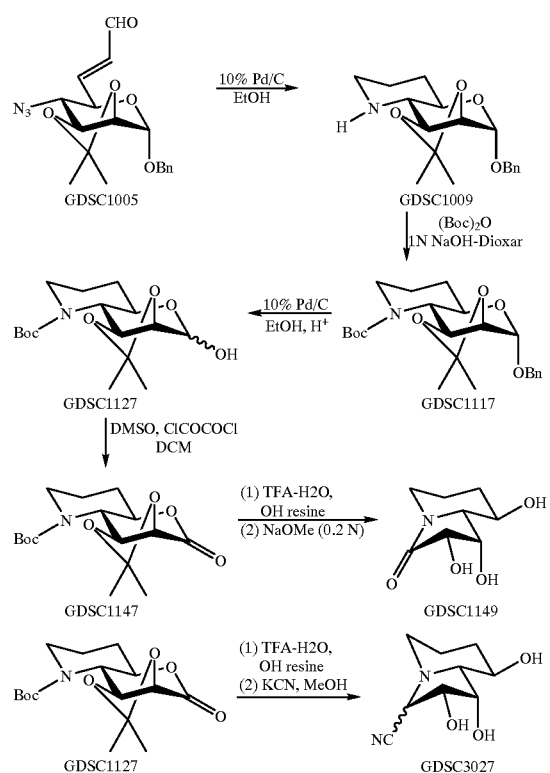

Example 5

Inhibition of Golgi α-mannosidase II and Lysosomal α-mannosidase by Compounds of the Invention The compounds of the invention and swainsonine were added (10 μl) into 96 well Elisa plates followed by the addition of 200 mM sodium acetate pH 5.6 and 25 μl of 10 mM p-nitrophenyl α-D-mannospyranoside. 15 μl of α-mannosidase (Sigma 38 U/ml) was added to each well and the plates were incubated for 60 min at 37° C. The reaction was stopped by the addition of 50 μl of 0.5M sodium carbonate and formation of p-nitrophenol was measured with a plate set at 405 nM. The effects of the compounds and swainsonine on lysosomal mannosidase were measured by adding (10 μl) of the compounds into 96 well Elisa plates followed by the addition of 200 mM sodium acetate pH 5.0 and 25 μl of 10 mM p-nitrophenyl α-D-mannospyranoside. 15 μl of lysosomal mannosidase (about 8 mM/mL) was added to each well and the plates were incubated for 60 min at 37° C. The reaction was stopped by the addition of 50 μl of 0.5M sodium carbonate and formation of p-nitrophenol was measured with a plate set at 405. The mannosidase II and lysosomal mannosidase activity of compounds of the formula I of the invention are shown in Table 1.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Compound | Mannosidase II Activity (μM) | Lysosomal Mannosidase Activity (μM) |
|---|---|---|
| Swainsonine | 0.080 ± 0.033 | 0.080 ± 0.079 |
| (5S)-5-Hydroxymethyl-swainsonine (GD 46) | 0.638 ± 0.22 | 1.485 ± 0.455 |
| (5S)-5-Methylswainsonine (GD 28) | 0.738 ± 0.32 | 0.316 ± 0.0759 |
| (5S)-5-Ethylswainsonine (GD 38) | 0.768 ± 0.12 | 0.360 ± 0.3132 |
| (5R)-5-Methylswainsonine (GD 20) | 0.847 ± 0.33 | 2.296 ± 1.128 |
| (5S)-5-benzyloxymethyl swainsonine (GD 91) | 0.989 ± 0.44 | 3.23 ± 0.268 |
| (5R)-5-benzyloxymethyl swainsonine (GD 42) | 1.140 ± 0.33 | 0.164 ± 0.0491 |
| 3-hydroxymethyl-swainsonine (EJH-4-264) | 1.28 ± 0.8 (3) | 1.70 ± 0.5 (9) |
| 3-hydroxymethyl-swainsonine (EJH-4-263) | 1.83 ± 1.3 (3) | 39.13 ± 16.3 (10) |
| (5R)-5-Hydroxymethyl swainsonine GD 45 | 2.051 ± 0.65 | 0.705 ± 0.309 |
| (5R)-5-Methylswainsonine formate salt (GD 19) | 2.455 ± 1.53 | 1.45 ± 0.071 |
| (5R)-8-epi-5-methylswainsonine GD 37 | 17.223 ± 3.87 | 28.157 ± 7.847 |
| Ethyl(1R,2R,5S,6S,8S,8aR)-1,2,8-trihydroxy-5-methyloctahydro-6-indolizinecarboxylate (GD 36) | 18.700 ± 4.95 | 120.275 ± 32.173 |
| (5S,6S)-6-hydroxymethyl-5-methylswainsonine (GD 40) | 19.88 ± 7.29 | 62.378 ± 17.892 |
| (5R,6R)-6-hydroxymethyl-5-methylswainsonine (GD 44) | 25.167 ± 10.41 | 24.482 ± 7.618 |
| (1S,2S,3R/S,8R,8aS)-3-cyano-1,2,8-Trihydroxyoctahydro-5-indolizine(GD 92) | 30.850 ± 12.23 | 30.150 ± 1.202 |
| ethyl(5R,6R)-5-methylswainsonine-6-carboxylate(GD 84) | 1000 | 1500 ± 707 |
| (1S,2R,8R,8aS)-1,2,8-Trihydroxyhexahydo-3(2H)-indolizinone(GD 35) | 1030 | 1087 |
| (1S,8R,8aS)-1,5,6,7,8,8a-Hexahydro-1,2,3,8-indolizinetetraol | No detectable inhibition | No detectable inhibition |

We claim:

1. A compound of the formula I

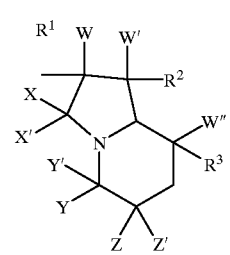

wherein (1) $R^1$, $R^2$ and $R^3$ are hydrogen;

(2) W, W' and W" are the same or different and represent hydroxyl, alkoxy, thiol, thioalkyl, thioaryl, halo or amino;

(3) X, X', Y, Y', Z, and Z' are the same or different and represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amine, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —$SR^9$ wherein $R^9$ is alkyl, cycloalkyl, alkenyl, alkynyl, or unsaturated monocyclic hydrocarbons, and —OR where R is alkenyl, alkynyl, or unsaturated monocyclic hydrocarbons; or (i) X and Y, X' and Y, X' and Y, or X' and Y' may together form a carbocyclic, or heterocyclic ring, or Y and Z, Y and Z', or Y' and Z' may together form a carbocyclic, or heterocyclic ring;

(ii) one or more of X and X' together, Y and Y' together, and Z and Z' together may form a spiro ring; or (iii) one or more of X and X' together, Y and Y' together, and Z and Z' together represent =O, =S, or =$NR^4$ wherein $R^4$ is hydrogen, alkyl, cycloalkyl, alkenyl, alkynyl, unsaturated monocyclic hydrocarbons, aryl, alkoxy, hydroxyl, or =$CR^5R^6$ wherein $R^5$ and $R^6$ are the same or different and represent hydrogen, alkyl, cycloalkyl, alkenyl, alkynyl, unsaturated monocyclic hydrocarbons, or aryl;

with the proviso that X, X', Y, Y', and Z, Z' cannot all be hydrogen, and when X, X', Z and Z' are hydrogen, and W, W', and W" are hydroxyl, Y and Y' together cannot be =O or one of Y and Y' cannot be alkoxy, and pharmaceutically acceptable salts and optically active and racemic forms thereof.

2. A compound of the formula I

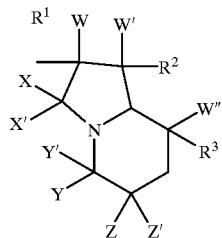

wherein (1) $R^1$, $R^2$ and $R^3$ are the same or different and represent hydrogen, alkyl, cycloalkyl, alkenyl, alkynyl, unsaturated monocyclic hydrocarbons, or aryl;

(2) W, W' and W" represent hydroxyl;

(3) X, X', Y, Y', Z, and Z' are the same or different and represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amine, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —$SR^9$ wherein $R^9$ is alkyl, cycloalkyl, alkenyl, alkynyl, or unsaturated monocyclic hydrocarbons, and —OR where R is alkenyl, alkynyl, or unsaturated monocyclic hydrocarbons; or (i) X and Y, X' and Y, X' and Y, or X' and Y' may together form a carbocyclic, or heterocyclic ring, or Y and Z, Y and Z', or Y' and Z' may together form a carbocyclic, or heterocyclic ring;

(ii) one or more of X and X' together, Y and Y' together, and Z and Z' together may form a spiro ring; or (iii) one or more of X and X' together, Y and Y' together, and Z and Z' together represent =O, =S, or =$NR^4$ wherein $R^4$ is hydrogen, alkyl, cycloalkyl, alkenyl, alkynyl, unsaturated monocyclic hydrocarbons, aryl, alkoxy, hydroxyl, or =$CR^5R^6$ wherein $R^5$ and $R^6$ are the same or different and represent hydrogen, alkyl, cycloalkyl, alkenyl, alkynyl, unsaturated monocyclic hydrocarbons, or aryl;

with the proviso that X, X', Y, Y', and Z, Z' cannot all be hydrogen, and when X, X', Z and Z' are hydrogen, and W, W', and W" are hydroxyl, Y and Y' together cannot be =O or one of Y and Y' cannot be alkoxy;

and pharmaceutically acceptable salts and optically active and racemic forms thereof.

3. A compound of the formula I

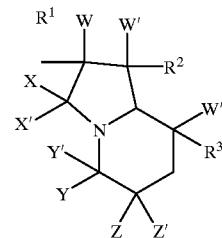

wherein (1) $R^1$, $R^2$ and $R^3$ are hydrogen;

(2) W, W' and W" are the same or different and represent alkoxy, thiol, thioalkyl, thioaryl, halo or amino, or one or more of W and W' and W' and W" together form a carbocyclic or heterocyclic ring;

(3) X, X', Y and Y' are hydrogen, and Z, and Z' are the same or different and represent alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amine, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —$SR^9$ wherein $R^9$ is alkyl, cycloalkyl, alkenyl, alkynyl, or unsaturated monocyclic hydrocarbons, and —OR where R is alkenyl, alkynyl, or unsaturated monocyclic hydrocarbons; or (i) Z and Z' together may form a spiro ring; or (iii) Z and Z' together represent =O, =S, or =$NR^4$ wherein $R^4$ is hydrogen, alkyl, cycloalkyl, alkenyl, alkynyl, unsaturated monocyclic hydrocarbons, aryl, alkoxy, hydroxyl, or =$CR^5R^6$ wherein $R^5$ and $R^6$ are the same or different and represent hydrogen, alkyl, cycloalkyl, alkenyl, alkynyl, unsaturated monocyclic hydrocarbons, or aryl;

and pharmaceutically acceptable salts and optically active and racemic forms thereof.

4. A compound as claimed in claim 1, wherein W, W', and W" represent hydroxyl, and X and X' represent hydrogen.

5. A compound as claimed in claim 1, wherein W, W', and W" represent hydroxyl, and Z and Z' represent hydrogen.

6. A compound as claimed in claim 1 wherein W, W', and W" represent hydroxyl, and Y and Y' represent hydrogen.

7. A compound of the formula I

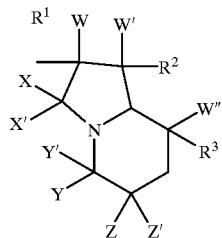

wherein (1) $R^1$, $R^2$, and $R^3$ are the same or different and represent hydrogen, alkyl, cycloalkyl, alkenyl, alkynyl, unsaturated monocyclic hydrocarbons, aryl or $R^1$ and $R^2$ together or $R^2$ and $R^3$ together form a carbocyclic or heterocylic ring;

(2) W, W' and W" are the same or different and represent hydroxyl, alkoxy, thiol, thioalkyl, thioaryl, halo or amino, or one or more of W and W' and W' and W" together form a carbocyclic or heterocyclic ring;

or one or more of $R^1$ and W, $R^2$ and W', and $R^3$ and W" form a spiro ring system;

(3) one of Y and Y' represents methyl, ethyl, phenyl, benzyl, trifluoromethyl, hydroxymethyl or benzyloxymethyl, and the other of Y and Y', and X, X', Z, and Z' which may be the same or different, represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amine, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —$SR^9$ wherein $R^9$ is alkyl, cycloalkyl, alkenyl, alkynyl, or unsaturated monocyclic hydrocarbons, and —OR where R is alkenyl, alkynyl, or unsaturated monocyclic hydrocarbons; or (i) one or more of X and X' together, and Z and Z' together may form a spiro ring; or (iii) one or more of X and X' together, and Z and Z' together represent =O, =S, or =$NR^4$ wherein $R^4$ is hydrogen, alkyl, cycloalkyl, alkenyl, alkynyl, unsaturated monocyclic hydrocarbons, aryl, alkoxy, hydroxyl, or =$CR^5R^6$ wherein $R^5$ and $R^6$ are the same or different and represent hydrogen, alkyl, cycloalkyl, alkenyl, alkynyl, unsaturated monocyclic hydrocarbons, or aryl;

with the proviso that X, X', Y, Y', and Z, Z' cannot all be hydrogen;

and pharmaceutically acceptable salts and optically active and racemic forms thereof.

8. A compound of the formula I

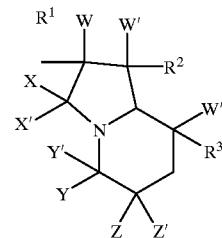

wherein (1) $R^1$, $R^2$, and $R^3$ are the same or different and represent hydrogen, alkyl, cycloalkyl, alkenyl, alkynyl, unsaturated monocyclic hydrocarbons, aryl or $R^1$ and $R^2$ together or $R^2$ and $R^3$ together form a carbocyclic or heterocylic ring;

(2) W, W' and W" are the same or different and represent hydroxyl, alkoxy, thiol, thioalkyl, thioaryl, halo or amino, or one or more of W and W' and W' and W" together form a carbocyclic or heterocyclic ring;

or one or more of $R^1$ and W, $R^2$ and W', and $R^3$ and W" form a spiro ring system;

(3) one of X and X' represents thiomethyl, fluoromethyl, or methoxy and the other of X and X', and Y, Y', Z, and Z' which may be the same or different represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amines, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —$SR^9$ wherein $R^9$ is alkyl, cycloalkyl, alkenyl, alkynyl, or unsaturated monocyclic hydrocarbons, and —OR where R is alkenyl, alkynyl, or unsaturated monocyclic hydrocarbons, (i) Y and Z, Y and Z', or Y' and Z' may together form a carbocyclic, or heterocyclic ring;

(ii) one or more of Y and Y' together, and Z and Z' together may form a spiro ring; or (iii) one or more of Y and Y' together, and Z and Z' together represent =O, =S, or =$NR^4$ wherein $R^4$ is hydrogen, alkyl, cycloalkyl, alkenyl, alkynyl, unsaturated monocyclic hydrocarbons, aryl, alkoxy, hydroxyl, or =$CR^5R^6$ wherein $R^5$ and $R^6$ are the same or different and represent hydrogen, alkyl, cycloalkyl, alkenyl, alkynyl, unsaturated monocyclic hydrocarbons, or aryl;

with the proviso that X, X', Y, Y', and Z, Z' cannot all be hydrogen;

and pharmaceutically acceptable salts and optically active and racemic forms thereof.

9. A compound of the formula I

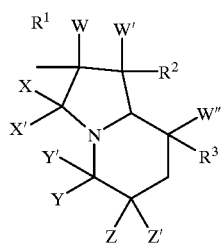

I wherein (1) R¹ and R² are the same or different and represent hydrogen, alkyl, cycloalkyl, alkenyl, alkynyl, unsaturated monocyclic hydrocarbons, aryl or R¹ and R² together form a carbocyclic or heterocylic ring, and R³ represents halogen (2) W and W' are the same or different and represent hydroxyl, alkoxy, thiol, thioalkyl, thioaryl, halo or amino, or W and W' together form a carbocyclic or heterocyclic ring, and W" represents halogen;

(3) X, X', Y, Y', Z, and Z' are the same or different and represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amine, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —SR⁹ wherein R⁹ is alkyl, cycloalkyl, alkenyl, alkynyl, or unsaturated monocyclic hydrocarbons, and —OR where R is alkenyl, alkynyl, or unsaturated monocyclic hydrocarbons; or (i) X and Y, X' and Y, X and Y', or X' and Y' may together form a carbocyclic, or heterocyclic ring, or Y and Z, Y and Z', or Y' and Z' may together form a carbocyclic, or heterocyclic ring;

(ii) one or more of X and X' together, Y and Y' together, and Z and Z' together may form a spiro ring; or (iii) one or more of X and X' together, Y and Y' together, and Z and Z' together represent =O, =S, or =NR⁴ wherein R⁴ is hydrogen, alkyl, cycloalkyl, alkenyl, alkynyl, unsaturated monocyclic hydrocarbons, aryl, alkoxy, hydroxyl, or =CR⁵R⁶ wherein R⁵ and R⁶ are the same or different and represent hydrogen, alkyl, cycloalkyl, alkenyl, alkynyl, unsaturated monocyclic hydrocarbons, or aryl;

with the proviso that X, X', Y, Y', and Z, Z' cannot all be hydrogen;

and pharmaceutically acceptable salts and optically active and racemic forms thereof.

10. A compound of the formula I

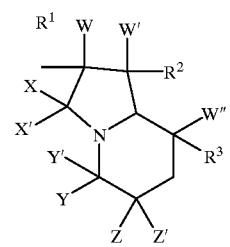

I wherein (1) R¹, R², and R³ are the same or different and represent hydrogen, alkyl, cycloalkyl, alkenyl, alkynyl, unsaturated monocyclic hydrocarbons, aryl or R¹ and R² together or R² and R³ together form a carbocyclic or heterocylic ring;

(2) W, W' and W" are the same or different and represent hydroxyl, alkoxy, thiol, thioalkyl, thioaryl, halo or amino, or one or more of W and W' and W' and W" together form a carbocyclic or heterocyclic ring;

or one or more of R¹ and W, R² and W', and R³ and W" form a spiro ring system;

(3) Y and Y' represent halogen, X, X', Z, and Z' may be the same or different and represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epoxide, alkoxy or aryloxy amine, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —SR⁹ wherein R⁹ is alkyl, cycloalkyl, alkenyl, alkynyl, or unsaturated monocyclic hydrocarbons, and —OR where R is alkenyl, alkynyl, or unsaturated monocyclic hydrocarbons; or (i) one or more of X and X' together, and Z and Z' together may form a spiro ring; or (ii) one or more of X and X' together, and Z and Z' together represent =O, =S, or =NR⁴ wherein R⁴ is hydrogen, alkyl, cycloalkyl, alkenyl, alkynyl, unsaturated monocyclic hydrocarbons, aryl, alkoxy, hydroxyl, or =CR⁵R⁶ wherein R⁵ and R⁶ are the same or different and represent hydrogen, alkyl, cycloalkyl, alkenyl, alkynyl, unsaturated monocyclic hydrocarbons, or aryl;

with the proviso that X, X', Z, and Z' cannot all be hydrogen;

and pharmaceutically acceptable salts and optically active and racemic forms thereof.

11. A compound of the formula I wherein

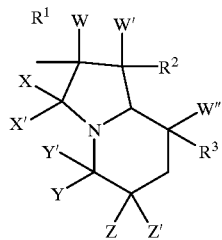

(1) $R^1$, $R^2$ and $R^3$ are the same or different and represent hydrogen, alkyl, cycloalkyl, alkenyl, alkynyl, unsaturated monocyclic hydrocarbons, aryl, or $R^1$ and $R^2$ together or $R^2$ and $R^3$ together form a carbocyclic or heterocylic ring;

(2) W, W' and W" are the same or different and represent hydroxyl, alkoxy, thiol, thioalkyl, thioaryl, halo or amino, or one or more of W and W' and W' and W" together form a carbocyclic or heterocyclic ring;

or one or more of $R^1$ and W, $R^2$ and W', and $R^3$ and W" form a spiro ring system;

(3) wherein one of Y and Y' is hydrogen and the other of Y and Y' is methyl, and one of Z and Z' is hydroxymethyl, —COCH$_2$CH$_3$, —CN, —CH$_2$NH$_2$, —CH$_2$NHAc, or —CH$_2$NHCR$^{60}$=NH where $R^{60}$ is alkyl or aryl; and the other of Z and Z', and X and X' which may be the same or different, represent hydrogen, alkyl, cycloalkyl, alkenyl, alkynyl, unsaturated monocyclic hydrocarbons, aryl, alkoxy, aryloxy, hydroxyl, thiol, thioaryl, amino, ammonium, halogen, carboxylic acid or esters or thioesters thereof, ketone, aldehyde, carbonate, carbamate, amide, azide, imide, imine, imidazole, acetal, ketal, nitrile, diazo, nitro, hydrazine, hydrazide, hydrazone, hydroxamic acid, hydroxylamine, epooxide, alkoxy or aryloxy amines, sulfate, sulfonic or sulfinic acid or esters thereof, sulfonamide, phosphate or phosphonate acids or esters thereof, silyl, sulfoxide, sulfone, oxime, guanidino, phosphonate, thioamide, thiocarbamate, thiocyanate, thioketone, thiourea, thioethers, triazole, urea, xanthate, cyano, nitrile, —SR$^9$ wherein $R^9$ is alkyl, cycloalkyl, alkenyl, alkynyl, or unsaturated monocyclic hydrocarbons, and —OR where R is alkyl is alkyl, cycloalkyl, alkenyl, alkynyl, or unsaturated monocyclic hydrocarbons; or (ii) X and X' together may form a spiro ring; or (iii) X and X' together represent =O, =S, or =NR$^4$ wherein $R^4$ is hydrogen, alkyl, cycloalkyl, alkenyl, alkynyl, unsaturated monocyclic hydrocarbons, aryl, alkoxy, hydroxyl, or =CR$^5$R$^6$ wherein $R^5$ and $R^6$ are the same or different and represent hydrogen, alkyl, cycloalkyl, alkenyl, alkynyl, unsaturated monocyclic hydrocarbons, or aryl;

with the proviso that X, X', Y, Y', and Z, Z' cannot all be hydrogen, and salts and optically active and racemic forms of a compound of the formula I.

12. A compound as claimed in claim 1 wherein X, X', Y, Y', Z, and Z' are the same or different and represent hydrogen, halogen, alkyl, aryl, alkoxy, aryloxy, amino, amide, thiol, thioalkyl, thioaryl, —COOH, esters of carboxylic acids, thioesters, —CH$_2$OR$^{52}$ where $R^{52}$ represents alkyl or aryl, —CONR$^{70}$R$^{71}$ where $R^{70}$ and $R^{71}$ are the same or different and represent hydrogen, alkyl, or aryl, —COCH$_2$CH$_3$, —CN, —CH$_2$NH$_2$, —CH$_2$NHAc, or —CH$_2$NHCR$^{60}$=NH where $R^{60}$ is alkyl or aryl.

13. A compound as claimed in claim 1, wherein W, W', W" are the same and represent hydroxyl.

14. A compound as claimed in claim 1, wherein W, W' and W" represent hydroxyl, and X, X', Z and Z' represent hydrogen.

15. A compound as claimed in claim 1, wherein W, W' and W" represent hydroxyl, Z and Z' represent hydrogen, one of X and X', which may be substituted, is alkyl, aryl, alkoxy, hydroxyl, thiol, thioalkyl, thioaryl, amino, halogen, carboxylic acid esters, thiol esters, benzyl, pyridinyl, —CH$_2$OR$^{52}$ where $R^{52}$ represents alkyl or aryl, and the other of X and X' is hydrogen, or X and X' together represent =O, and, one of Y and Y', which may be substituted, is alkyl, aryl, alkoxy, hydroxyl, thiol, thioalkyl, thioaryl, amino, halogen, carboxylic acid esters, thiol esters, —CH$_2$OR$^{52}$ where $R^{52}$ represents alkyl or aryl, benzyl, or and the other of Y and Y' is hydrogen.

16. A compound as claimed in claim 1, wherein W, W' and W" represent hydroxyl, Y and Y' represent hydrogen, X and X', which may be substituted, are the same or different and represent hydrogen, alkyl, aryl, alkoxy, hydroxyl, thiol, thioalkyl, thioaryl, amino, halogen, carboxylic acid esters, thiol esters, benzyl, or pyridinyl, or —CH$_2$OR$^{52}$ where $R^{52}$ represents alkyl or aryl, and Z and Z' are the same or different and represent alkyl, aryl, alkoxy, hydroxyl, thiol, thioalkyl, thioaryl, amino, halogen, carboxylic acid esters, thiol esters, benzyl, or pyridinyl, or CH$_2$OR$^{52}$ where $R^{52}$ represents alkyl or aryl, with the proviso that at least one of X and X' and at least one of Z and Z' cannot be hydrogen.

17. A compound as claimed in claim 1, wherein W, W' and W" represent hydroxyl, and X and X' represents hydrogen, Y, Y', Z, and Z' are the same or different and represent hydrogen, alkyl, aryl, alkoxy, hydroxyl, thiol, thioalkyl, thioaryl, amino, halogen, carboxylic acid esters, thiol esters, benzyl, pyridinyl, or —CH$_2$OR$^{50}$ where $R^{52}$ represents alkyl or aryl, with the proviso that at least one of Y and Y' and one of Z and Z' cannot be hydrogen.

18. A compound as claimed in claim 1, wherein W, W' and W" represent hydroxyl, and X, X', Z and Z' represent hydrogen, and one of Y and Y' represent hydrogen, alkyl, aryl, hydroxyl, thiol, thioalkyl, thioaryl, amino, halogen, carboxylic acid esters, thiol esters, benzyl, pyridinyl, or —CH$_2$OR$^{50}$ where $R^{50}$ represents alkyl or aryl, and the other of Y and Y' represents hydrogen, alkyl, aryl, hydroxyl, thiol, thioalkyl, thioaryl, amino, halogen, carboxylic acid esters, thiol esters, benzyl, pyridinyl, or —CH$_2$OR$^{50}$ where $R^{50}$ represents alkyl or aryl.

19. A compound as claimed in claim 1, wherein W, W' and W" represent hydroxyl, and Y, Y', Z and Z' represent hydrogen, and one of X and X' represents hydrogen, alkyl, aryl, alkoxy, hydroxyl, thiol, thioalkyl, thioaryl, amino, halogen, carboxylic acid esters, thiol esters, benzyl, pyridinyl, or —CH$_2$OR$^{50}$ where $R^{50}$ represents alkyl or aryl, and the other of X and X' represent hydrogen, alkyl, aryl, alkoxy, hydroxyl, thiol, thioalkyl, thioaryl, amino, halogen, carboxylic acid esters, thiol esters, benzyl, pyridinyl, or —CH$_2$OR$^{52}$ where $R^{52}$ represents alkyl or aryl, or X and X' together represent =O.

20. A compound as claimed in claim 1, wherein W, W' and W" represent hydroxyl, and Z and Z' represent hydrogen, and X and Y, X' and Y', X' and Y, or X and Y' together form a 6 member heterocyclic ring containing one or two of O, S, or N.

21. A compound as claimed in claim 1, wherein W, W' and W" represent hydroxyl, X, X', Z and Z' represent hydrogen, and one of Y and Y' represents methyl, ethyl, phenyl, or benzyl which may be substituted, preferably trifluoromethyl, hydroxymethyl, benzyloxymethyl, and the other of Y and Y' represent hydrogen.

22. A compound as claimed in claim 1, wherein W represents hydroxyl, and W' and W" represent halogen, X, X', Z and Z' represent hydrogen, and one of Y and Y' represents methyl, ethyl, phenyl, benzyl, trifluoromethyl, hydroxymethyl, or benzyloxymethyl, and the other of Y and Y' represents hydrogen.

23. A compound as claimed in claim 1, wherein one of Y and Y' is hydrogen and the other of Y and Y' is methyl, and one of Z and Z' is hydroxymethyl, $-COCH_2CH_2CH_3$, $-CN$, $-CH_2NH_2$, $-CH_2NHAc$, or $-CH_2NHCR^{60}=NH$ where $R^{60}$ is alkyl or aryl.

24. A compound as claimed in claim 1, wherein one of Y and Y' and one of Z and Z' represents alkyl, aryl, alkoxy, hydroxyl, thiol, thioalkyl, benzyl, pyridinyl, or $-CH_2OR^{52}$ where $R^{52}$ represents alkyl or aryl, which may be substituted, and the other of Y and Y' and Z and Z' represents hydrogen.

25. A compound as claimed in claim 1, wherein one of Z and Z' is $-CONR^{70}R^{71}$ where $R^{70}$ and $R^{71}$ are the same or different and represent hydrogen, alkyl, or aryl, $-COOH$, $-COOC_2H_5$, methyl, or $CH_2OH$, or Z and Z' together form a spiro ring.

26. A compound as claimed in claim 1, wherein X and Y form a carbocyclic or heterocyclic ring of the formula $R^{75}-R^{76}-R^{77}-R^{78}-R^{79}$ where $R^{75}$ and $R^{79}$ are part of the swainsonine skeleton and one or more of $R^{76}$, $R^{77}$, and $R^{78}$ represent CH, $CH_2$, O, S, or N.

27. A compound as claimed in claim 1, which is (5R)-5-methylswainsonine, (5R)-5-methylswainsonine formate salt, (5S)-5-methylswainsonine (5R)-8-Epi-5-methylswainsonine, (5S)-5-ethylswainsonine, (5S,6S)-6-hydroxymethyl-5-methylswainsonine; (5R)-5-benzyloxymethylswainsonine, (5R,6R)-6-hydroxymethyl-5-methylswainsonine,(5R)-5-hydroxymethylswainsonine, (5S)-5-hydroxymethylswainsonine, (5R,6R)-6-hydroxymethyl-5-methyl swainsonine, (5S)-5-benzyloxymethylswainsonine, or (5S)-5-benzyloxymethylswainsonine.

28. A pharmaceutical formulation comprising a compound as claimed in claim 1 as an active agent, and a pharmaceutically acceptable carrier, excipient or diluent.

29. A method for stimulating the immune system, treating proliferative disorders, or microbial infections in a patient, comprising administering an effective amount of a compound as claimed in claim 1.

30. A method for stimulating the immune system, treating proliferative disorders, or microbial infections in a patient, comprising administering to the patient an effective amount of a compound as claimed in claim 1, wherein:

W, W' and W" represent hydroxyl, Y, Y', Z and Z' represent hydrogen, and one of X and X' represents methyl, phenyl, or benzyl which may be substituted, and the other of X and X' represent hydrogen;

W, W' and W" represent hydroxyl, X, X', Z and Z' represent hydrogen, and one of Y and Y' represents methyl, ethyl, phenyl, or benzyl which may be substituted, and the other of Y and Y' represents hydrogen; or W, W' and W" represent hydroxyl, and Y and Y' represent hydrogen, X and X' are the same or different and represent hydrogen, alkyl, aryl, alkoxy, hydroxyl, thiol, thioalkyl, thioaryl, amino, halogen, carboxylic acid esters, thiol esters, benzyl, or pyridinyl, or $-CH_2OR^{52}$ where $R^{52}$ represents alkyl or aryl, which may be substituted, and one of Z and Z' are the same or different and represent alkyl, aryl, alkoxy, hydroxyl, thiol, thioalkyl, thioaryl, amino, halogen, carboxylic acid esters, thiol esters, benzyl, or pyridinyl, or $CH_2OR^{52}$ where $R^{52}$ represents alkyl or aryl, with the proviso that at least one of X and X' and at least one of Z and Z' cannot be hydrogen.

* * * * *